US012653783B2

(12) United States Patent
Olefsky et al.

(10) Patent No.: US 12,653,783 B2
(45) Date of Patent: Jun. 16, 2026

(54) COMPOSITIONS COMPRISING miR-690 AND METHODS THEREFOR

(71) Applicant: The Regents of the University of California, Oakland, CA (US)

(72) Inventors: Jerrold M. Olefsky, Solana Beach, CA (US); Wei Ying, San Diego, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 499 days.

(21) Appl. No.: 18/017,377

(22) PCT Filed: Jul. 21, 2021

(86) PCT No.: PCT/US2021/042664
§ 371 (c)(1),
(2) Date: Jan. 20, 2023

(87) PCT Pub. No.: WO2022/020534
PCT Pub. Date: Jan. 27, 2022

(65) Prior Publication Data
US 2023/0293434 A1 Sep. 21, 2023

Related U.S. Application Data

(60) Provisional application No. 63/055,636, filed on Jul. 23, 2020.

(51) Int. Cl.
| | |
|---|---|
| *A61K 9/127* | (2025.01) |
| *A61K 31/7105* | (2006.01) |
| *A61P 1/16* | (2006.01) |
| *A61P 3/10* | (2006.01) |
| *A61P 5/50* | (2006.01) |
| *C12N 15/88* | (2006.01) |

(52) U.S. Cl.
CPC .......... *A61K 9/127* (2013.01); *A61K 31/7105* (2013.01); *A61P 1/16* (2018.01); *A61P 3/10* (2018.01); *A61P 5/50* (2018.01); *C12N 15/88* (2013.01)

(58) Field of Classification Search
None
See application file for complete search history.

(56) References Cited

U.S. PATENT DOCUMENTS

| | | | | |
|---|---|---|---|---|
| 2013/0143314 A1* | 6/2013 | Shiels | ............... | G01N 33/5061 |
| | | | | 435/320.1 |
| 2017/0296627 A1* | 10/2017 | Tarnopolsky | ...... | A61K 38/1866 |

FOREIGN PATENT DOCUMENTS

| | | | | |
|---|---|---|---|---|
| EP | 2860255 | | 4/2015 | |
| EP | 2860255 A1 * | | 4/2015 | ............. A61K 9/127 |
| JP | 2018198611 | * | 12/2018 | |
| JP | 2018198611 A | * | 12/2018 | |
| WO | 2022020534 | | 1/2022 | |

OTHER PUBLICATIONS

Gold et al, Apr. 13, 2020, (https://www.healthcentral.com/condition/diabetes-treatment). (Year: 2020).*
"International Application Serial No. PCT US2021 042664, International Search Report mailed Nov. 22, 2021", 4 pgs.
"International Application Serial No. PCT US2021 042664, Written Opinion mailed Nov. 22, 2021", 6 pgs.
"International Application Serial No. PCT US2021 042664, International Preliminary Report on Patentability mailed Feb. 2, 2023", 8 pgs.
Dahlmans, "Evaluation of Muscle microRNA Expression in Relation to Human Peripheral Insulin Sensitivity: A Cross-Sectional Study in Metabolically Distinct Subject Groups", 1-10. Frontiers in Physiology (8), (Sep. 21, 2017), 10 pgs.
Menikdiwela, "Role of microRNA 690 in Mediating Angiotensin II Effects on Inflammation and Endoplasmic Reticulum Stress", 1-20. Cells (9), (May 26, 2020), 22 pgs.
Ying, Wei, "MiR-690, an exosomal-derived miRNA from M2-polarized macrophages, improves insulin sensitivity in obese mice", Cell Metabolism, vol. 33, (Apr. 6, 2021), 24 pages.

* cited by examiner

*Primary Examiner* — Celeste A Roney
(74) *Attorney, Agent, or Firm* — SCHWEGMAN LUNDBERG & WOESSNER, P.A.

(57) ABSTRACT

Compositions comprising miR-690 and methods of employing the compositions are provided.

20 Claims, 25 Drawing Sheets

Figure 2
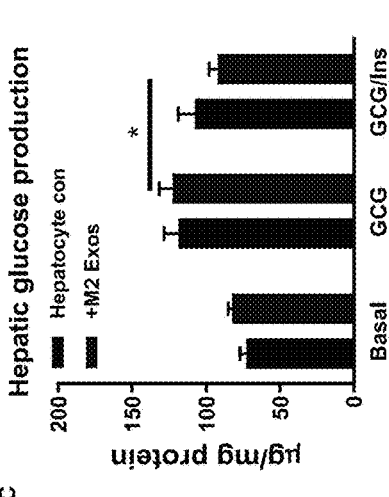
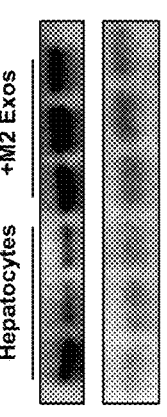
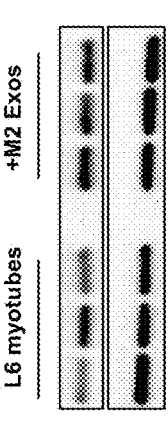
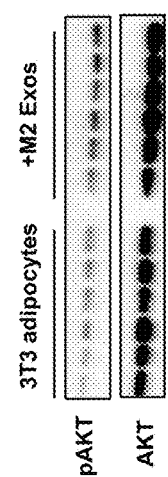

Figure 3
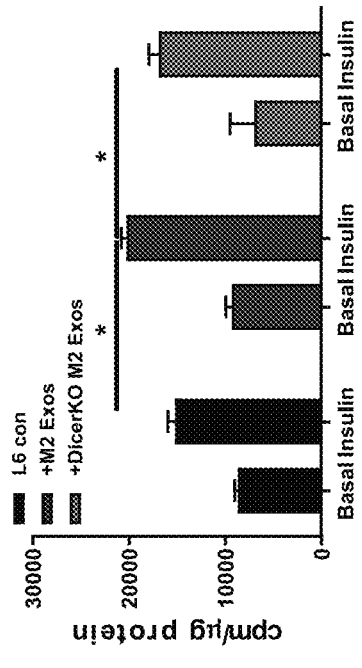
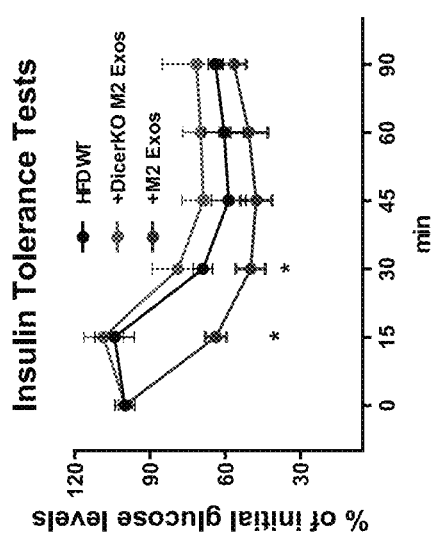
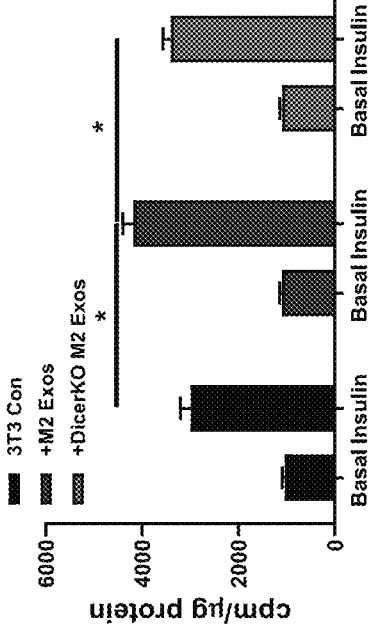
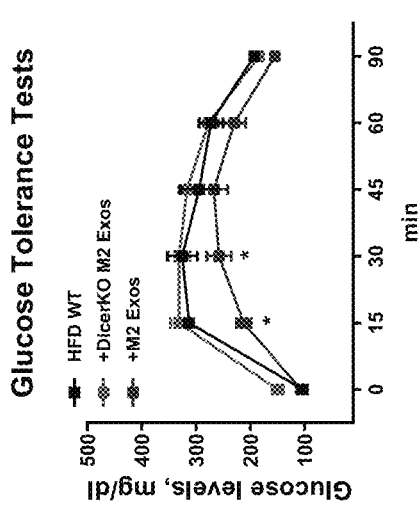

Figure S1

Figure S1. Characteristics of M2 Exos, related to Figure 1. Electron microscopy analysis (A), NanoSight analysis (B), and expression of EV-associated markers (C) of M2 Exos. (D) The appearance of PKH26 red fluorescence in metabolic tissues after 16 hours intravenous injection of PKH26-labeled M2 Exos.

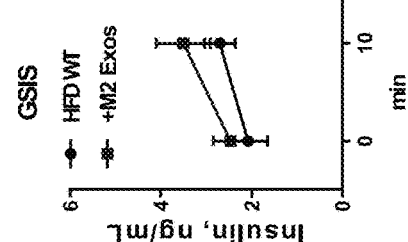
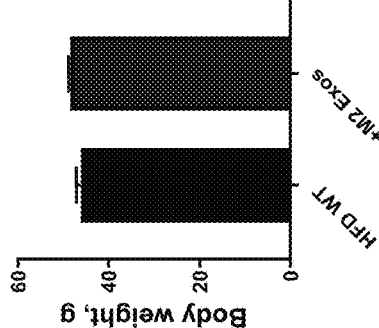
Figure 9
Figure S2
Figure S2. In vivo effects of M2 Exos, related to Figure 2. Effect of M2 Exos on body weight (A) and glucose-stimulated insulin secretion (GSIS) (B) of HFD/obese recipient mice. Data are presented as mean ± SEM. n=6 per group (A and B).

Figure 10
Figure S3
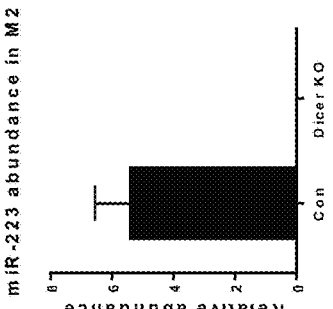
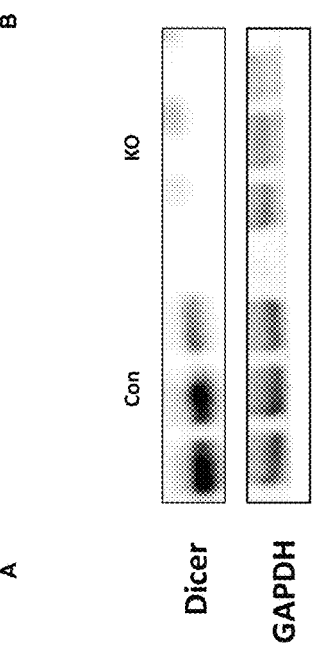
Figure S3. Effect of dicer knockout on miRNA abundance in BMDM Exos, related to Figure 3. (A) Confirmation of dicer knockout in BMDMs derived from LysMcre+Dicer^{f/f} mice. (B) miR-223 abundance within M2 Exos derived from DicerKO M2 BMDMs. Data are presented as mean ± SEM. n=4 per group (B).

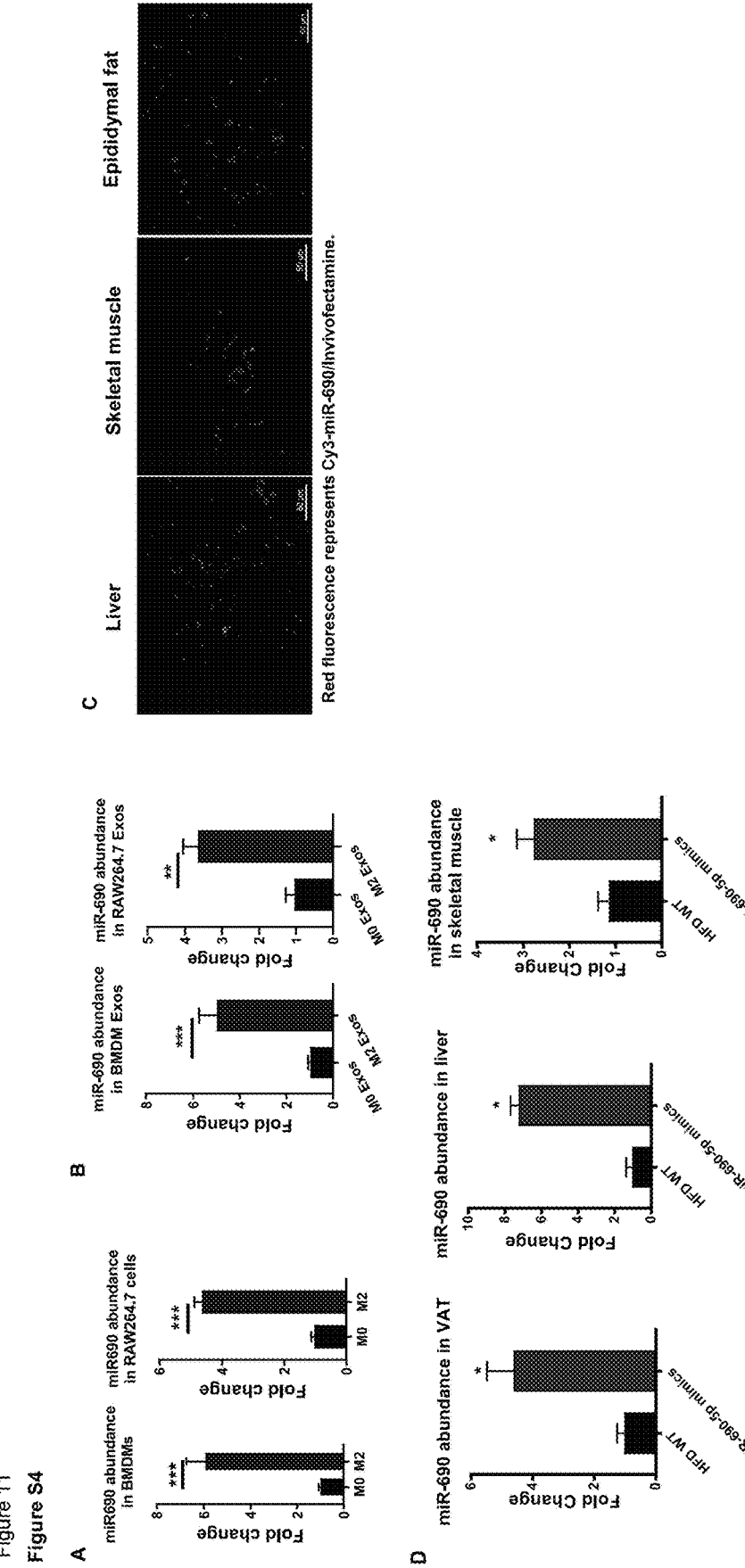

Red fluorescence represents Cy3-miR-690/Invivofectamine.

Figure S4. Effects of in vivo overexpression of miR-690-5p, related to Figure 4. (A) miR-690 abundance in BMDMs and RAW264.7 cells. (B) The levels of miR-690 in Exos derived from BMDMs or RAW264.7 cells. (C) The presence of Cy3 red fluorescence in metabolic tissues of HFD/obese mice after intravenous injection of Cy3-miR-690-containing BMDM EVs. (D) miR-690 expression in metabolic tissues after treatment of miR-690/Invivofectamine. Data are presented as mean ± SEM. n=4 per group (A, B, and D). *P<0.05, P<0.01, *P<0.001, Student's t test.

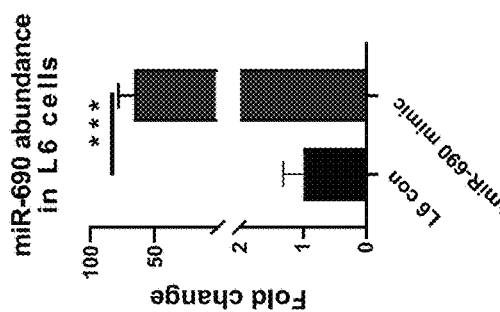
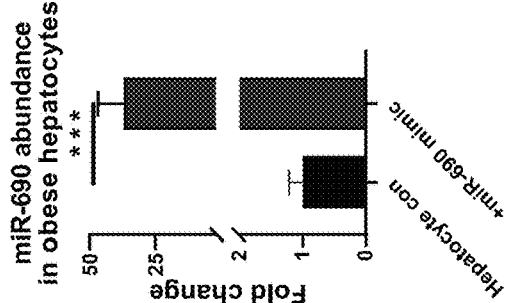
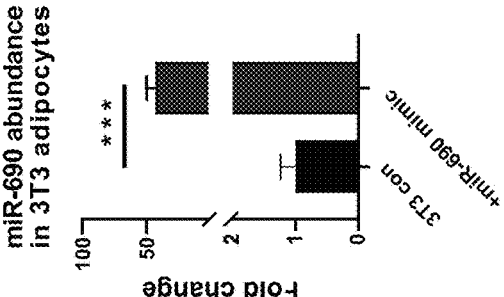
Figure 12
Figure S5
Figure S5. Effect of miR-690 on cellular insulin responses, related to Figure 5. Expression of miR-690 in 3T3-L1 adipocytes (A), hepatocytes (B), and L6 myotubes (C) after transfection of miR-690 mimic. Data are presented as mean ± SEM. n=4 per group (A-C). ***P<0.001, Student's t test.

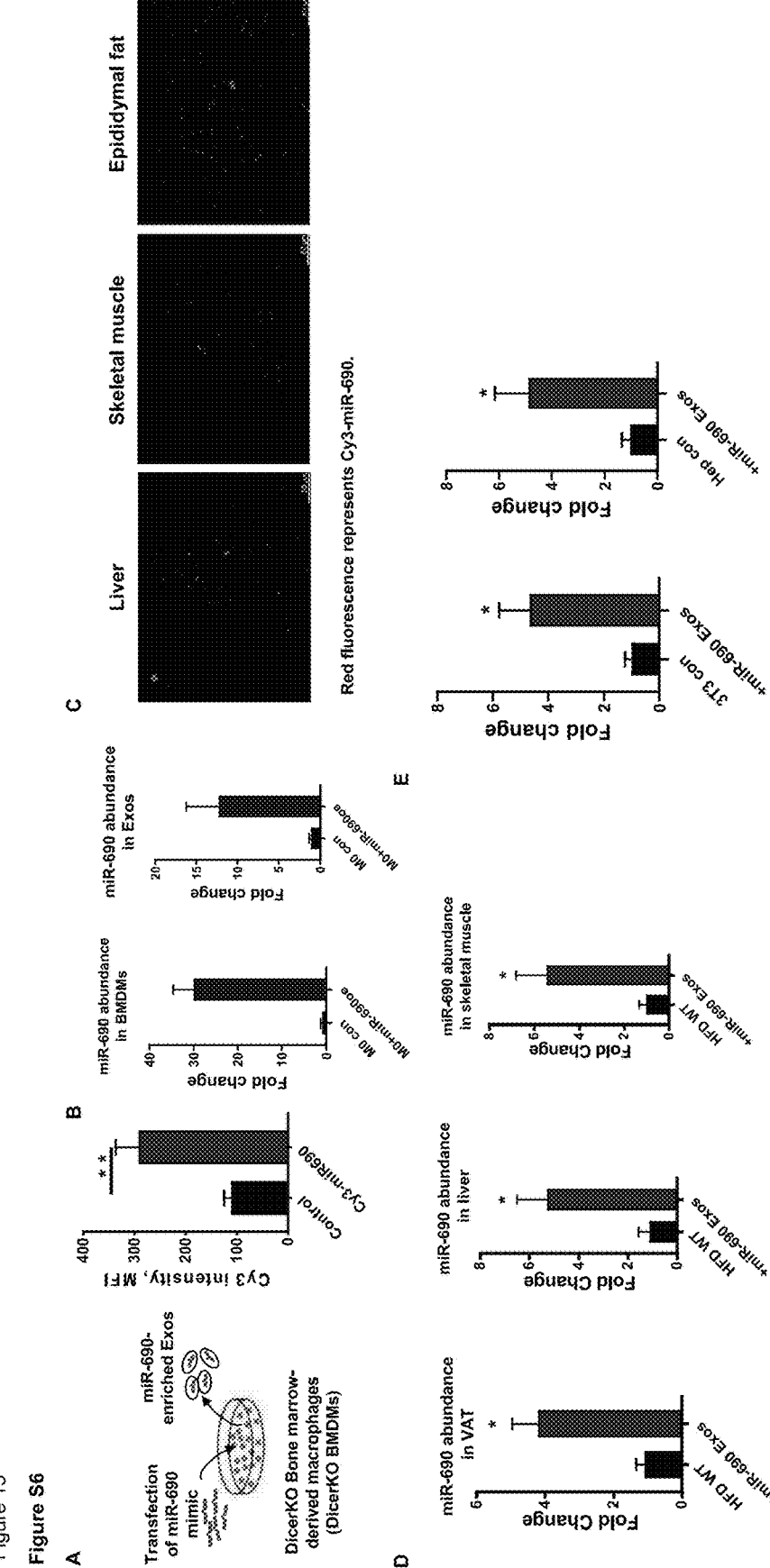

Figure S6. miR-690-5p is enriched in M2 Exos, related to Figure 6. (A) The packaging of Cy3-miR-690 into BMDM Exos. (B) The abundance of miR-690 in BMDMs and their Exos after overexpression of miR-690. (C) The appearance of Cy3 red fluorescence in metabolic tissues of HFD/obese recipient mice after treatment of Cy3-miR-690 encapsulated by Invivofectamine. (D) After 5 weeks injection, the abundance of miR-690 in the metabolic tissues of HFD/obese recipient mice. (E) miR-690 abundance after coculturing miR-690 enriched Exos with 3T3-L1 adipocytes or hepatocytes. Data are presented as mean ± SEM. n=4 per group (A, B, D, and E). *P<0.05, Student's t test.

Figure 14
Figure S7
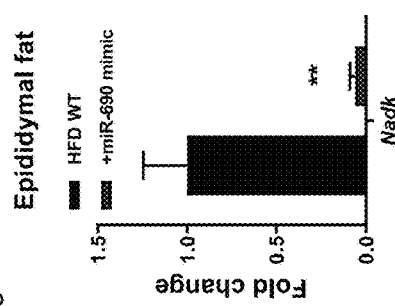
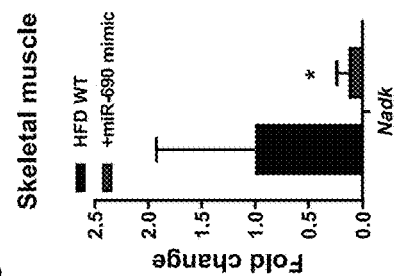
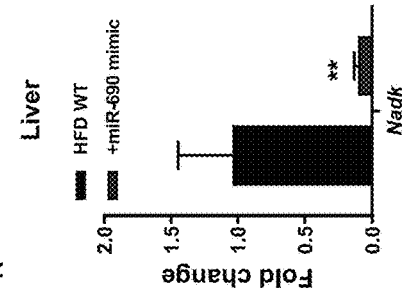
Figure S7. Effect of miR-690 on Nadk expression, related to Figure 7. miR-690 abundance in liver (A), skeletal muscle (B), and epididymal fat (C) after treatment of miR-690/Invivofectamine. Data are presented as mean ± SEM. n=4 per group (A-C). *P<0.05, **P<0.01, Student's t test.

Fig. 15

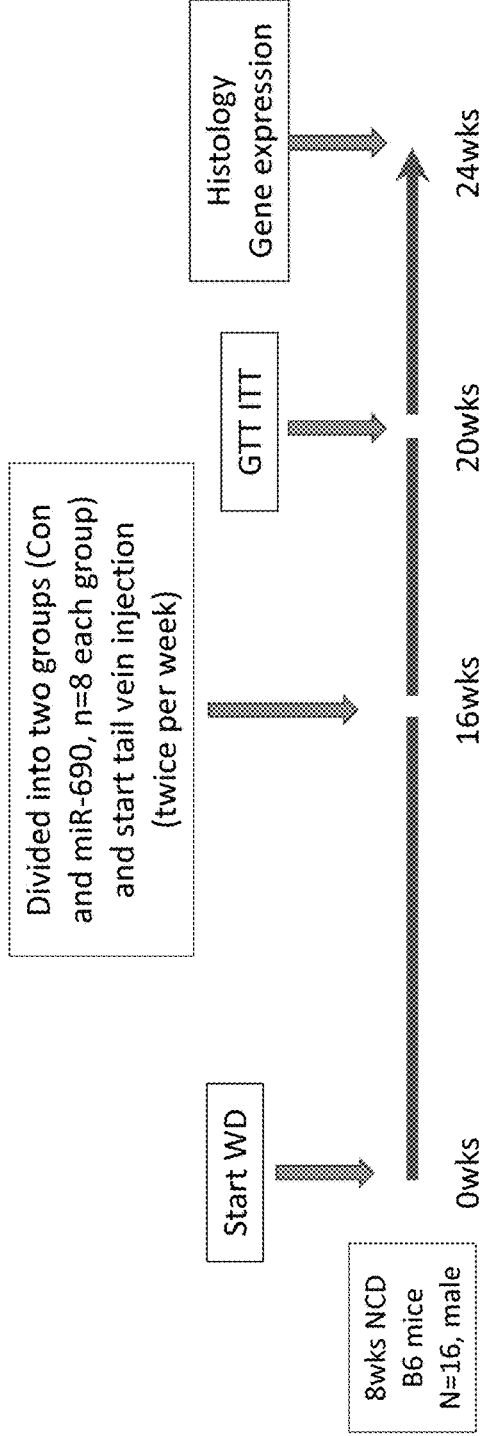

16 weeks Western diet fed WT mice were intravenously injected the nanoparticles containing either scrambled miRNA or miR-690 mimic (5 nmol/mouse, twice injection per week). After 4 weeks treatment, these mice were used for glucose or insulin tolerance tests. Finally, the liver of these mice were used for histology analysis and gene expression analysis after 24 weeks Western diet feeding.

Increased levels of liver miR-690 expression after treatment

The expression of miR-690 (A) and NADK (B) in the livers of NASH WT mice after 8 weeks treatment with the nanoparticles containing miR-690 mimic. NASH control mice were treated with the nanoparticles containing scrambled miRNA. Data are presented as mean ± SEM. * $P < 0.05$, Student's t test.

miR-690 treatment promotes glucose tolerance and insulin sensitivity in NASH mice.

Glucose tolerance (A) and insulin sensitivity (B) in NASH WT mice after 8 weeks treatment with the nanoparticles containing miR-690 mimic. NASH control mice were treated with the nanoparticles containing scrambled miRNA. Data are presented as mean ± SEM. * P < 0.05, ** P<0.01, Student's t test.

miR-690 treatment reduces steatosis in NASH mice.

H&E staining analysis in the livers of NASH WT mice after 8 weeks treatment with the nanoparticles containing miR-690 mimic. NASH control mice were treated with the nanoparticles containing scrambled miRNA.

Fig. 19 miR-690 treatment reduces liver lipid content in NASH mice

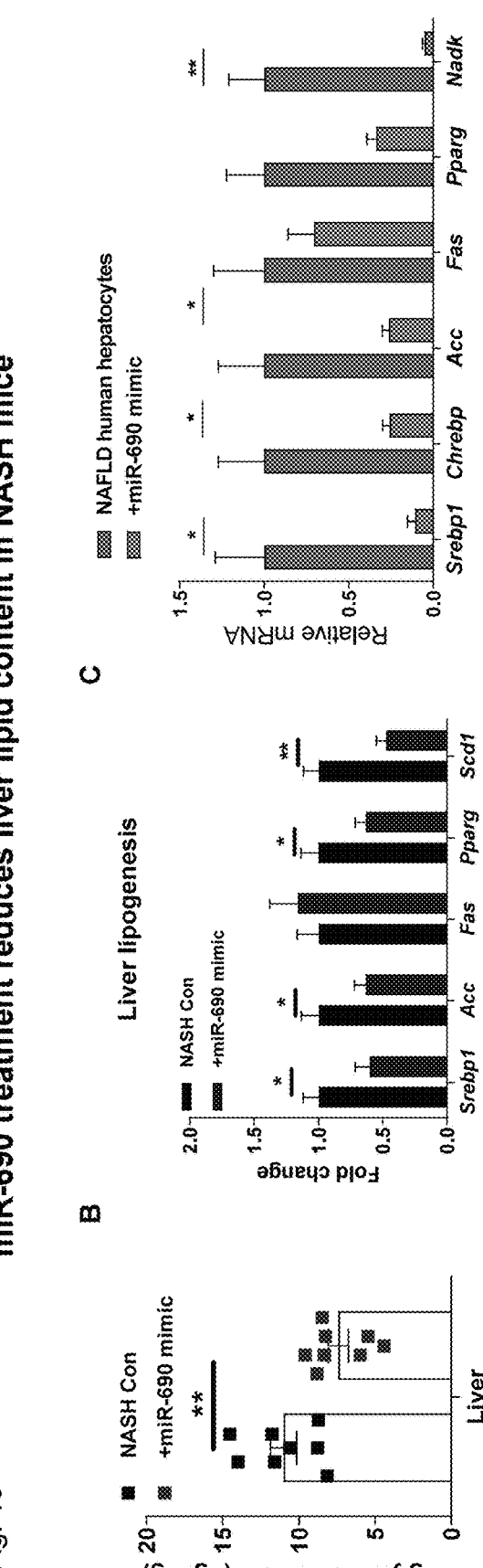

Triglyceride levels (A) and lipogenesis-related key gene abundance (B) in the livers of NASH WT mice after 8 weeks treatment with the nanoparticles containing miR-690 mimic. C, Effects of miR-690 overexpression on the expression of lipogenesis-related key genes in NAFLD human hepatocytes. NASH control mice or NAFLD human hepatocytes were treated with the nanoparticles containing scrambled miRNA. Data are presented as mean ± SEM. * P< 0.05, ** P<0.01, Student's t test.

Fig. 20 miR-690 treatment reduces tissue inflammation.

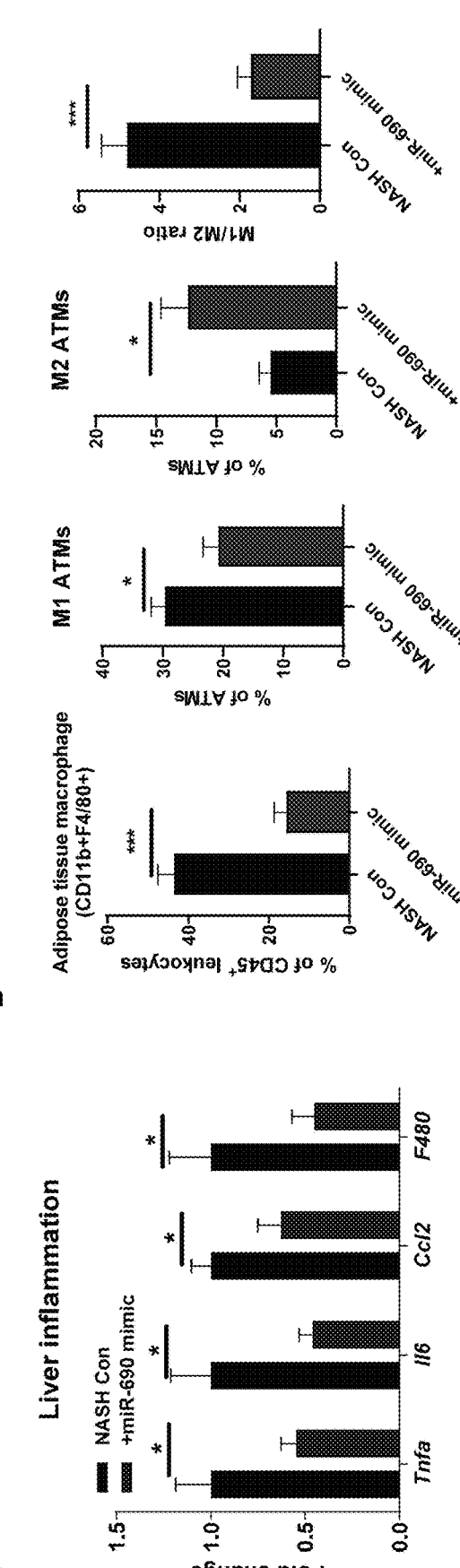

Levels of proinflammatory mediators in the liver (A) and population of adipose tissue macrophages (B) of NASH WT mice after 8 weeks treatment with the nanoparticles containing miR-690 mimic. NASH control mice were treated with the nanoparticles containing scrambled miRNA. M1, CD11b+F4/80+CD11c+CD206-; M2, CD11b+F4/80+CD11c-CD206+. Data are presented as mean ± SEM. * $P < 0.05$, *** $P < 0.001$, Student's t test.

Fig. 21 miR-690 treatment induces Kupffer cell recovery and decreases recruited hepatic macrophages (RHMs) in NASH mice.

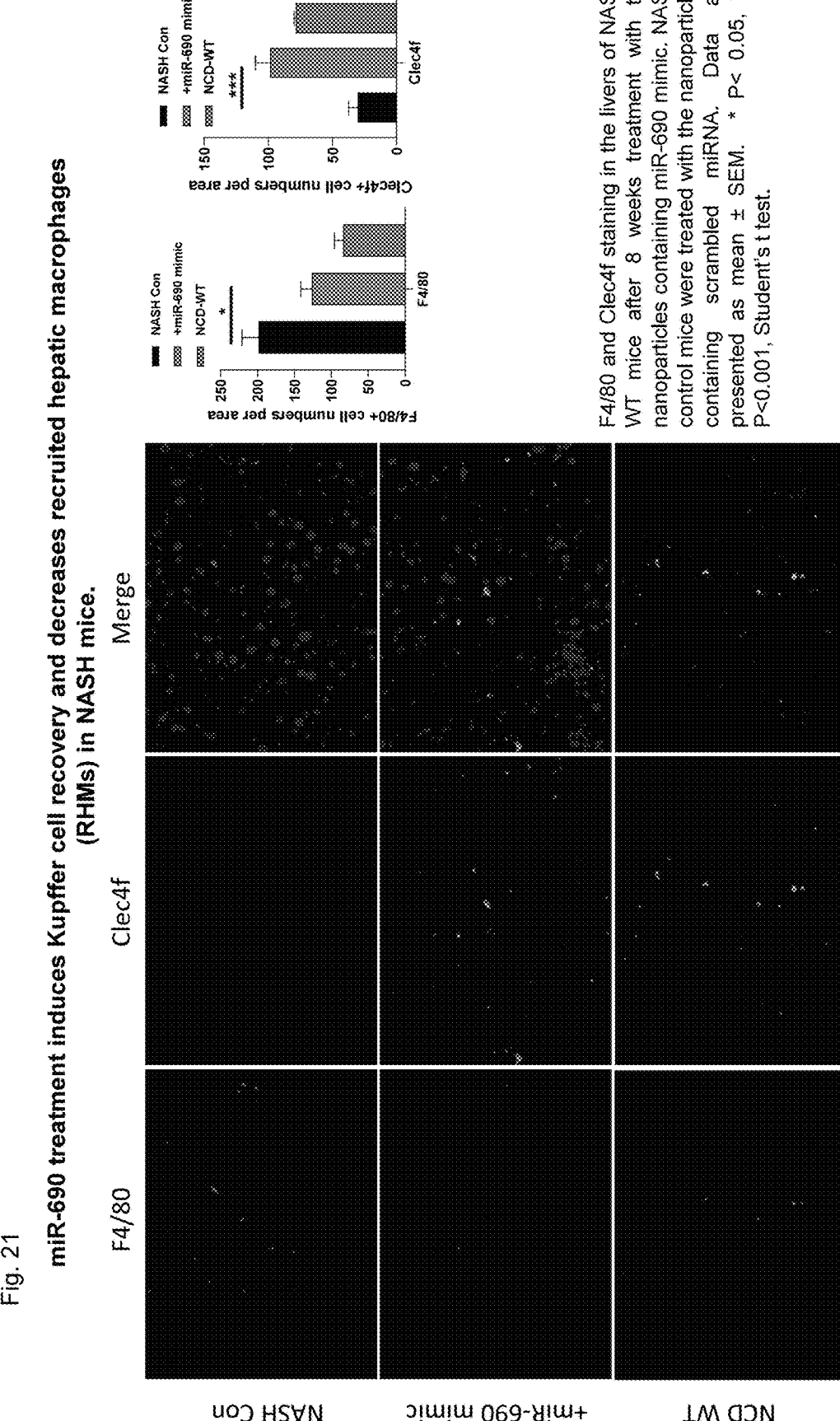

F4/80 and Clec4f staining in the livers of NASH WT mice after 8 weeks treatment with the nanoparticles containing miR-690 mimic. NASH control mice were treated with the nanoparticles containing scrambled miRNA. Data are presented as mean ± SEM. * P< 0.05, *** P<0.001, Student's t test.

miR-690 treatment increases anti-inflammatory macrophages in NASH mice.

Staining of F4/80 and CD206 in the livers of NASH WT mice after 8 weeks treatment with the nanoparticles containing miR-690 mimic. NASH control mice were treated with the nanoparticles containing scrambled miRNA. Data are presented as mean ± SEM. * P< 0.05, Student's t test.

miR-690 treatment reduces fibrosis in NASH mice.

Sirius red staining analysis of the livers from NASH WT mice after 8 weeks treatment with the nanoparticles containing miR-690 mimic. NASH control mice were treated with the nanoparticles containing scrambled miRNA. Data are presented as mean ± SEM. ** P<0.01, Student's t test.

Histology analysis of liver samples

All the miR-690 treated samples were scored as fibrosis regression.

The fibrosis score in NASH WT mice after 8 weeks treatment with the nanoparticles containing miR-690 mimic. NASH control mice were treated with the nanoparticles containing scrambled miRNA. Data are presented as mean ± SEM. ** P<0.01, Student's t test.

Fig. 25 miR-690 treatment represses hepatic stellate cell (HSC) activation.

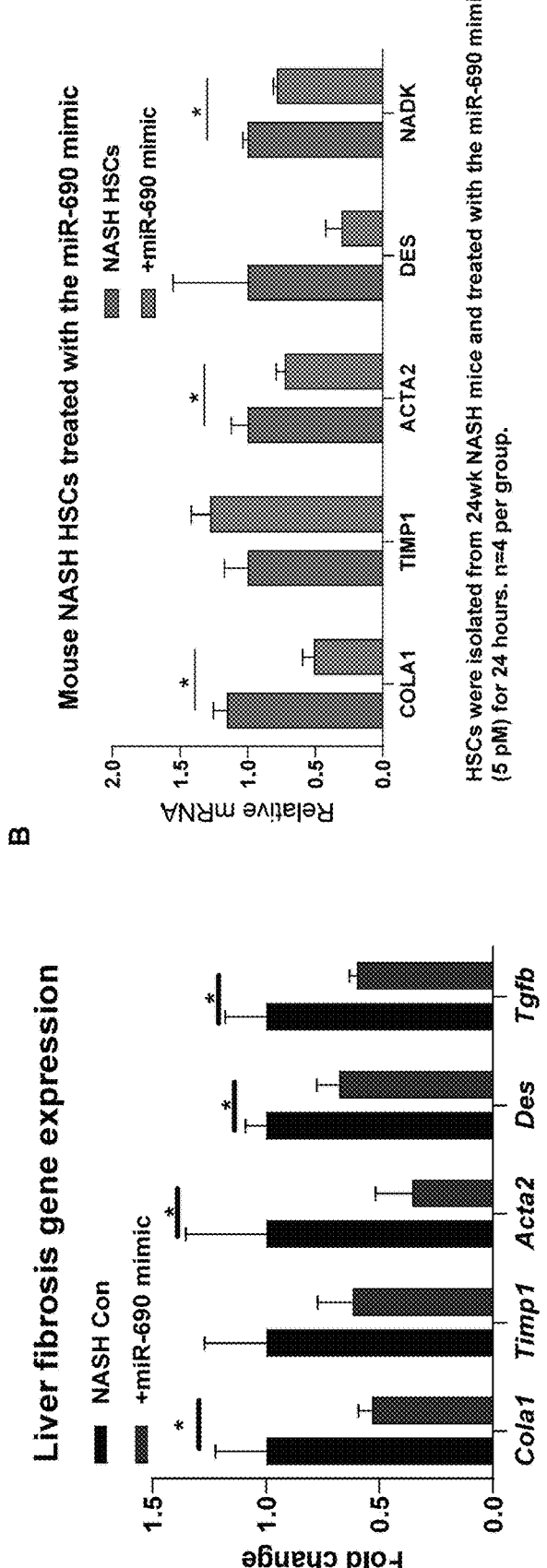

A, The expression of fibrogenic genes the liver of NASH WT mice after 8 weeks treatment with the nanoparticles containing miR-690 mimic. NASH control mice were treated with the nanoparticles containing scrambled miRNA. B, Effects of the miR-690 mimic on the abundance of fibrogenic genes in NASH mouse HSCs. Data are presented as mean ± SEM. ** $P<0.01$, Student's t test.

COMPOSITIONS COMPRISING miR-690 AND METHODS THEREFOR

CROSS-REFERENCE TO RELATED APPLICATIONS

This application is a U.S. National Stage Filing under 35 U.S.C. 371 from International Application No. PCT/US2021/042664, filed on Jul. 21, 2021, and published as WO 2022/020534 A1 on Jan. 27, 2022, which claims the benefit of the filing date of U.S. application No. 63/055,636, filed on Jul. 23, 2020, the disclosure of each of which is incorporated by reference herein.

STATEMENT OF GOVERNMENT RIGHTS

This invention was made with government support under K99DK115998, DK063491 and DK101395 awarded by the National Institutes of Health. The government has certain rights in the invention.

BACKGROUND

Insulin resistance is an antecedent defect in the great majority of patients with Type 2 diabetes mellitus (T2DM) (Kahn et al., 2006; Lee et al., 2018; Roden and Shulman, 2019; Romeo et al., 2012). Obesity is the main driver of insulin resistance in humans worldwide and the ongoing obesity epidemic is driving a parallel rise in the prevalence of T2DM (Johnson and Olefsky, 2013; Ogden et al., 2016). It has become clear that obesity-induced chronic, subacute tissue inflammation, particularly when it occurs in adipose tissue and liver, can cause insulin resistance (Hotamisligil, 2017; Saltiel and Olefsky, 2017). As a hallmark of tissue inflammation, obesity results in the accumulation of proinflammatory macrophages in these tissues, acting as the major source of inflammatory mediators such as tumor necrosis factor, galectin 3, and other cytokines (Hotamisligil et al., 1995; Hotamisligil et al., 1996; Li et al., 2016; Lumeng et al., 2007a; Lumeng et al., 2007b; Weisberg et al., 2003). Consistent with these, many studies have demonstrated the importance of macrophage-mediated inflammation as a cause of insulin resistance (Lee et al., 2018).

In the healthy lean state, macrophages residing in key metabolic tissues such as adipose tissue, liver, and skeletal muscle preferentially display the alternatively activated, anti-inflammatory M2-like phenotype (Fink et al., 2014; Lumeng et al., 2007a; Morinaga et al., 2015). Eosinophils, regulatory T cells, and adipocytes are sources of interleukin 4 (IL4) and IL13 which polarizes macrophages toward the M2 state (Kang et al., 2008; Qiu et al., 2014; Tiemessen et al., 2007; Wu et al., 2011). The ability of M2-like macrophages to regulate tissue remodeling and inflammation resolution underpins their role in maintaining systemic insulin sensitivity and glucose homeostasis. For example, previous studies have shown that the depletion of tissue resident M2-like macrophages in mice, by depletion of eosinophils or knockout of PPARγ, exacerbates obesity-induced glucose intolerance and insulin resistance (Odegaard et al., 2007; Wu et al., 2011). However, obesity significantly changes tissue microenvironmental factors, such as increased chemokine secretion and elevated free fatty acid levels, all of which can switch macrophage activation to the more proinflammatory M1-like state (Kanda et al., 2006; Kratz et al., 2014; Li et al., 2015; Xu et al., 2013). Thus, it is challenging to enhance the proportion of M2 macrophages in the context of obesity. One mechanism by which M2 macrophages exert beneficial effects involves IL10 secretion, and previous studies have shown that IL10 ablation in mice does not exacerbate obesity-induced glucose intolerance and insulin resistance (den Boer et al., 2006; Rajbhandari et al., 2018; Saraiva and O'Garra, 2010). In addition to cytokines, emerging evidence has demonstrated that exosomes (Exos) play roles in modulating metabolic homeostasis (Crewe et al., 2018; Guay et al., 2019; Whitham et al., 2018; Ying et al., 2017).

SUMMARY

As disclosed herein, M2 polarized bone marrow-derived macrophages (BMDMs) were shown to secrete miRNA-containing exosomes (Exos), which improve glucose tolerance and insulin sensitivity in obese mice. Depletion of the miRNA cargo blocked the ability of M2 BMDM Exos to enhance insulin sensitivity, indicating that miRNAs are responsible for these beneficial effects of BMDM Exos. It was found that miR-690 was highly expressed in M2 macrophage Exos and functioned as an insulin sensitizer that can increase insulin action both in vivo and in vitro. Packaging a miR-690 mimic, e.g., nucleic acid having 5'-aaaggcuagg-cucacaaccaaa-3' (miR-690-5p; SEQ ID NO:1) into miRNA-depleted BMDMs generated Exos that recapitulated the effects of M2 macrophage Exos on metabolic phenotypes. The present results show that transcripts for nicotinamide adenine dinucleotide kinase (Nadk) are a bona tide target mRNA of miR-690, and the miR-690-Nadk axis plays a role in modulating insulin signaling. Taken together, miR-690 likely is an insulin sensitizing agent for metabolic disease, e.g., to improve insulin sensitivity. In one embodiment, miR-690 may be employed for the treatment of insulin resistance, including type 2 diabetes or obesity-related insulin resistance disorders.

The disclosure provides a composition comprising a synthetic delivery vehicle comprising an insulin sensitizing amount of isolated miR-690. In one embodiment, the delivery vehicle comprises a nanoparticle or microparticle. In one embodiment, the delivery vehicle comprises a liposome. In one embodiment,
   the composition further comprises a pharmaceutically
      acceptable carrier.

In one embodiment, a method to inhibit Nadk expression in a mammal, comprising: administering to the mammal an effective amount of a composition comprising isolated miR-690 or a vector encoding miR-690.

In one embodiment, a method to inhibit or treat insulin resistance in a mammal, comprising administering to the mammal an effective amount of a composition comprising isolated miR-690 or a vector encoding miR-690.

In one embodiment, a method to enhance insulin sensitivity in a mammal, comprising administering to the mammal an effective amount of a composition comprising isolated miR-690 or a vector encoding miR-690.

In one embodiment, a method to treat metabolic disease in a mammal, comprising administering to the mammal an effective amount of a composition comprising isolated miR-690 or a vector encoding miR-690. In one embodiment, the disease is Type 2 diabetes, obesity-induced insulin resistance, a cardiovascular disease, a nonalcoholic fatty liver disease, or nonalcoholic steatohepatitis.

In one embodiment, a method to prevent Type 2 Diabetes in a mammal at risk of developing Type 2 diabetes, comprising administering to the mammal an effective amount of a composition comprising isolated miR-690 or a vector encoding miR-690.

In one embodiment, the mammal is a human. In one embodiment, the mammal has type 2 diabetes. In one embodiment, the mammal has obesity-related insulin resistance, In one embodiment, the mammal has nonalcoholic liver disease (NASH). In one embodiment, the mammal has polycystic ovarian syndrome. In one embodiment, the mammal is obese. In one embodiment, the composition comprises nanoparticles or microparticles. In one embodiment, the composition comprises liposomes. In one embodiment, the composition comprises a plasmid encoding miR-690. In one embodiment, the composition comprises isolated miR-690. In one embodiment, the composition comprises a recombinant virus encoding miR-690. In one embodiment, the virus is a recombinant adenovirus, retrovirus, lentivirus, herpesvirus or adeno-associated virus. In one embodiment, the amount reduces steatosis, In one embodiment, the amount reduces hepatic inflammation. In one embodiment, the amount reduces hepatic fibrosis. In one embodiment, the composition is systemically administered. In one embodiment, the composition is injected. In one embodiment, the composition is intravenously administered. In one embodiment, the composition is orally administered. In one embodiment, the composition is intramuscularly administered. In one embodiment, the composition is locally administered. In one embodiment, the composition is topically administered. In one embodiment, the composition is subcutaneously administered.

BRIEF DESCRIPTION OF THE FIGURES

FIGS. 2A-2F. M2 Exos enhance cellular insulin responses. Effects of M2 Exos on glucose uptake of 3T3-L1 adipocytes (A) and L6 myotubes (B) and hepatic glucose output (C) The abundance of insulin-stimulated AKT phosphorylation of 3T3-L1 adipocytes (D), L6 myotubes (E), and hepatocytes (F) after M2 Exos treatment. Data are presented as mean±SEM. n=6 per group (A-C). *P<0.05, Student's t test.

FIGS. 3A-3D. miRNAs are important cargoes for the M2 Exos effects. The glucose uptake of 3T3-Li adipocytes (A) and L6 myotubes (B) after treatment of either M2 Exos or DicerKO M2 Exos. Effects of DicerKO M2 Exos on glucose intolerance (C) and insulin resistance (D) of HFD/obese recipient mice. Data are presented as mean±SEM. n=6 per group (A-D). *P<0.05, Student's t test.

FIGS. 9A-9B. in vivo effects of M2 Exos, related to FIG. 2. Effect of M2 Exos on body weight (A) and glucose-stimulated insulin secretion (GSIS) (B) of HFD/obese recipient mice. Data are presented as mean±SEM. n=6 per group (A and B).

FIGS. 10A-10B. Effect of dicer knockout on miRNA abundance in BMDM Exos, related to FIG. 3. (A) Confirmation of dicer knockout in BMDMs derived from LysM-cre+Dicer$^{f/f}$ mice. (B) miR-223 abundance within M2 Exos derived from DicerKO M2 BMDMs. Data are presented as mean±SEM. n=4 per group (B).

FIGS. 11A-11D. Effects of in vivo overexpression of miR-690, related to FIG. 4. (A) miR-690 abundance in BMDMs and RAW264.7 cells. (B) The levels of miR-690 in Exos derived from BMDMs or RAW264.7 cells. (C) The presence of Cy3 red fluorescence in metabolic tissues of HFD/obese mice after intravenous injection of Cy3-miR-690-containing BMDM EVs. (D) miR-690 expression in metabolic tissues after treatment of miR-690/Invivofectamine. Data are presented as mean±SEM, n=4 per group (A, B, and D). *P<0.05, P<0.01, *P<0.001, Student's t test.

FIGS. 12A-12C. Effect of miR-690 on cellular insulin responses, related to FIG. 5. Expression of miR-690 in 3T3-L1 adipocytes (A), hepatocytes (B), and L6 myotubes (C) after transfection of miR-690 mimic. Data are presented as mean±SEM. n=4 per group (A-C).*P<0.001, Student's t test.

FIGS. 13A-13E. miR-690 is enriched in M2 Exos, related to FIG. 6. (A) The packaging of Cy3-miR-690 into BMDM Exos. (B) The abundance of miR-690 in BMDMs and their Exos after overexpression of miR-690. (C) The appearance of Cy3 red fluorescence in metabolic tissues of HFD/obese recipient mice after treatment of Cy3-miR-690 encapsulated by Invivofectamine. (D) After 5 weeks injection, the abundance of miR-690 in the metabolic tissues of HFD/obese recipient mice. (E) miR-690 abundance after coculturing miR-690 enriched Exos with 3T3-L1 adipocytes or hepatocytes. Data are presented as mean±SEM. n=4 per group (A, B, D, and E). *P<0.05, Student's t test.

FIGS. 14A-14C. Effect of miR-690 on Nadk expression, related to FIG. 7. miR-690 abundance in liver (A), skeletal muscle (B), and epididymal fat (C) after treatment of miR-690 mimic. Data are presented as mean±SEM. n=4 per group (A-C). *P<0.05, **P<0.01, Student's t test.

FIG. 15. 16 weeks Western diet fed WT mice were intravenously injected the nanoparticles containing either scrambled miRNA or miR-690 mimic (5 nmol/mouse, twice injection per week). After 4 weeks treatment, these mice were used for glucose or insulin tolerance tests. Finally, the liver of these mice were used for histology analysis and gene expression analysis after 24 weeks Western diet feeding.

FIGS. 16A-168. Increased levels of liver miR-690 expression aftertreatment. The expression of miR-690 (A) and NADK (B) in the livers of NASH WT mice after 8 weeks treatment with the nanoparticles containing miR-690 mimic. NASH control mice were treated with the nanoparticles containing scrambled miRNA. Data are presented as mean±SEM. *P<0.05, Student's t test.

FIGS. 19A-19C. miR-690 treatment reduces liver lipid content in NASH mice. Triglyceride levels (A) and lipogenesis-related key gene abundance (B) in the livers of NASH WT mice after 8 weeks treatment with the nanoparticles containing miR-690 mimic. C, Effects of miR-690 overexpression on the expression of lipogenesis-related key genes in NAFLD human hepatocytes. NASH control mice or NAFLD human hepatocytes were treated with the nanoparticles containing scrambled miRNA. Data are presented as mean±SEM. *P<0.05, **P<0.01, Student's t test.

FIGS. 20A-20B. miR-690 treatment reduces tissue inflammation. Levels of proinflammatory mediators in the liver (A) and population of adipose tissue macrophages (B) of NASH WT mice after 8 weeks treatment with the nanoparticles containing miR-690 mimic. NASH control mice were treated with the nanoparticles containing scrambled miRNA. M1, CD11b+F4/80+CD11c+CD206−; M2, CD11b+F4/80+CD11c−CD206+. Data are presented as mean±SEM. *P<0.05, ***P<0.001, Student's t test.

FIG. 21. miR-690 treatment induces Kupffer cell recovery and decreases recruited hepatic macrophages (RHMs) in NASH mice. F4/80 and Clec4f staining in the livers of NASH WT mice after 8 weeks treatment with the nanoparticles containing miR-690 mimic. NASH control mice were treated with the nanoparticles containing scrambled miRNA. Data are presented as mean±SEM. *P<0.05, ***P<0.001, Student's t test.

FIGS. 25A-25B. miR-690 treatment represses hepatic stellate cell (HSC) activation. A) The expression of fibrogenic genes the liver of NASH WT mice after 8 weeks treatment with the nanoparticles containing miR-690 mimic. NASH control mice were treated with the nanoparticles containing scrambled miRNA. B) Effects of the miR-690 mimic on the abundance of fibrogenic genes in NASH mouse HSCs. Data are presented as mean±SEM. **P<0.01, Student's t test.

Figure 1:
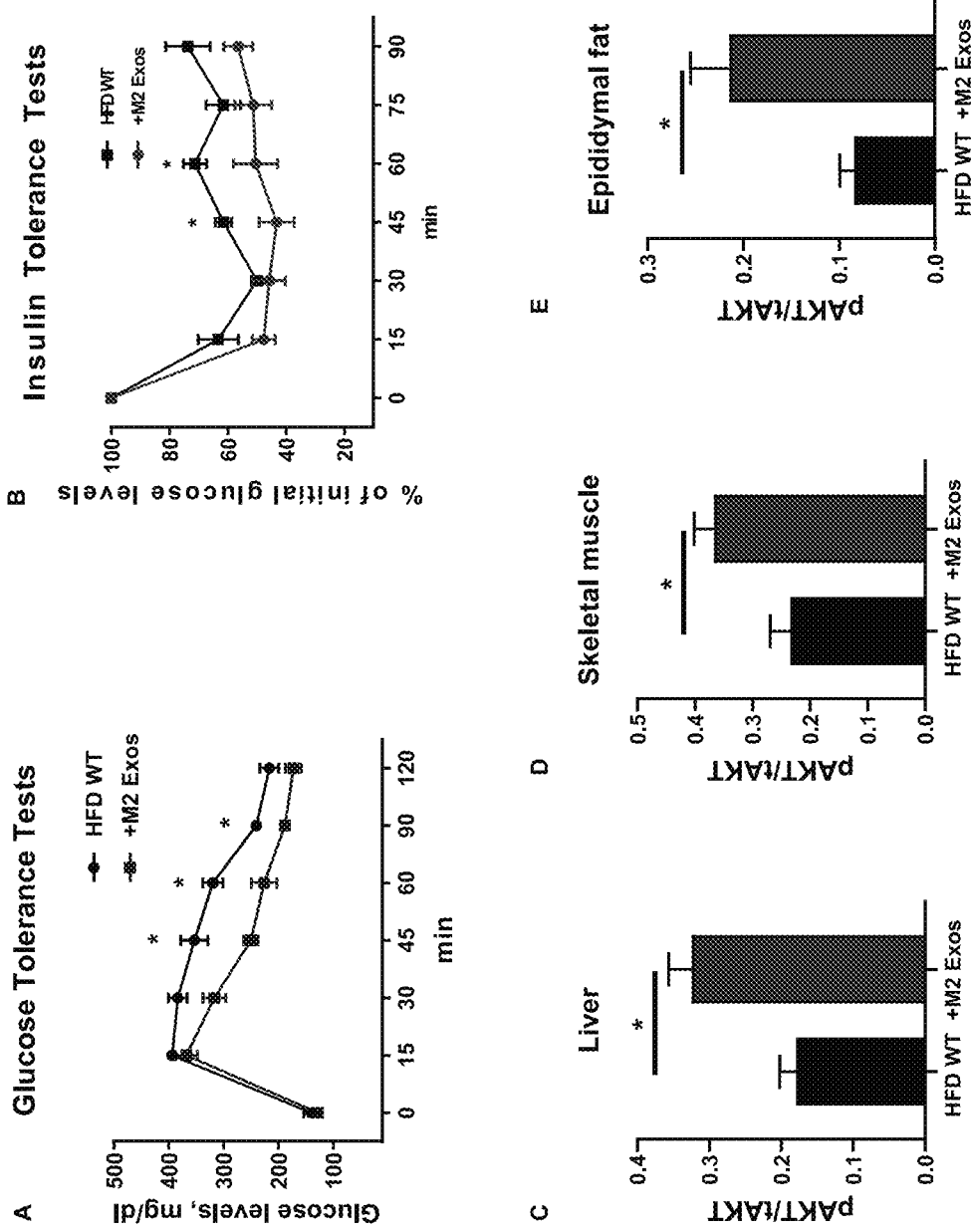
FIGS. 1A-1E. M2 Exos can improve obesity-induced glucose intolerance and insulin resistance. (A and B) Glucose and insulin tolerance tests of HFD/obese recipient mice after 4 weeks treatment of M2 Exos. The levels of insulin-stimulated AKT phosphorylation in liver (C), skeletal muscle (D), and epididymal fat (E) of obese recipient mice treated with M2 Exos. Data are presented as mean±SEM. n=6 per group (A-E). *P<0.05, Student's t test.

DETAILED DESCRIPTION miRNA-containing Exos obtained from lean adipose tissue macrophages (ATMs), the majority of which are anti-inflammatory M2-like cells, were shown to have insulin sensitizing effects (Ying et al., 2017). Thus, it was hypothesized that IL4/IL13-induced alternatively activated, anti-inflammatory M2-like macrophages secrete Exos containing miRNAs that can improve insulin sensitivity.

Herein, it is shown that M2 polarized bone marrow-derived macrophages (BMDMs) produce Exos which lead to improved glucose tolerance and insulin sensitivity, both in vivo and in vitro. Ablation of miRNAs blunted the ability of these Exos to exert their effects, indicating that miRNAs are functional cargo components within these Exos. Among the miRNAs highly enriched within M2 macrophage Exos, miR-690 is an insulin sensitizing miRNA, as evidenced by a significant improvement in cellular insulin signaling after in vitro or in vivo overexpression of miR-690. Treatment with macrophage Exos packed with miR-690 led to a robust enhancement in glucose tolerance and insulin sensitivity. Finally, Nadk is a bona fide target mRNA of miR-690 and Nadk can exert profound regulation on insulin sensitivity. Exemplary miRNA Sequences, Modifications and Compositions In one embodiment, miRNA based nucleic acids useful in the methods include but are not limited to 5'-AAAGGC-UAGGCUCACAACCAAA'3' (SEQ ID NO:1), as well as the corresponding DNA sequences or the complement thereof, and sequences having at least 90%, 92%, 95%, 96%, or 99% identity thereto. In one embodiment, the ribonucleotides or deoxyribonucleotides include one or more modified ribonucleotides or deoxyribonucleotides, e.g., modified phosphate linkages, modified sugars, modified nucleobases, or combinations thereof. In one embodiment, the precursor for the miRNA comprises tgtgttttg tggagctaat tggctgtatt aaagtgctag taagaaacat tctcctcca ctggagagat ggctcagctg ttaaaggcta ggctcacaac caaaatata (SEQ ID NO:10)

In one embodiment, miRNAs useful in the methods include but are not limited to 5'X1AAGGCUAX23" (SEQ ID NO:2), wherein X1 and X2 are independently absent or are from 1 to 20 ribonucleotides in length, e.g., X1 or X2 are 1, 2, 3, 4, 5, 6, 7, 8, 9, 10, or 15 ribonucleotides in length, as well as the corresponding DNA sequences, and sequences having at least 90%, 92%, 95%, 96%, or 99% identity thereto. In one embodiment, the ribonucleotides or deoxyribonucleotides include one or more modified ribonucleotides or deoxyribonucleotides, e.g., modified phosphate linkages, modified sugars, modified nucleobases, or combinations thereof.

In one embodiment, miRNAs useful in the methods include but are not limited to 5'X1X3AGGCUAX23' (SEQ ID NO:3), wherein X3 is not a, and wherein X1 and X2 are independently absent or are from 1 to 20 ribonucleotides in length, e.g., X1 or X2 are 1, 2, 3, 4, 5, 6, 7, 8, 9, 10, or 15 ribonucleotides in length, as well as the corresponding miRNA DNA sequences, and sequences having at least 90%, 92%, 95%, 96%, or 99% identity thereto. In one embodiment, the ribonucleotides or deoxyribonucleotides include one or more modified ribonucleotides or deoxyribonucleotides, e.g., modified phosphate linkages, modified sugars, modified nucleobases, or combinations thereof.

In one embodiment, miRNAs useful in the methods include but are not limited to 5'X1AX3AGGCUAX23' (SEQ ID NO:4), wherein X3 is not a, and X1 and X2 are independently absent or are from 1 to 20 ribonucleotides in length, e.g., X1 or X2 are 1, 2, 3, 4, 5, 6, 7, 8, 9, 10, or 15 ribonucleotides in length, as well as the corresponding miRNA DNA sequences, and sequences having at least 90%, 92%, 95%, 96%, or 99% identity thereto. In one embodiment, the ribonucleotides or deoxyribonucleotides include one or more modified ribonucleotides or deoxyribonucleotides, e.g., modified phosphate linkages, modified sugars, modified nucleobases, or combinations thereof.

In one embodiment, miRNAs useful in the methods include but are not limited to 5'X1AAX3GCUAX23' (SEQ ID NO:5), wherein X3 is not g, and X1 and X2 are independently absent or are from 1 to 20 ribonucleotides in length, e.g., X1 or X2 are 1, 2, 3, 4. 5, 6, 7. 8, 9, 10, or 15 ribonucleotides in length, as well as the corresponding DNA sequences, and sequences having at least 90%, 92%, 95%, 96%, or 99% identity thereto. In one embodiment, the ribonucleotides or deoxyribonucleotides include one or more modified ribonucleotides or deoxyribonucleotides, e.g., modified phosphate linkages, modified sugars, modified nucleobases, or combinations thereof.

In one embodiment, miRNAs useful in the methods include but are not limited to 5'X1AAGX3GCUAX23' (SEQ ID NO:6), wherein X3 is not g, and X1 and X2 are independently absent or are from 1 to 20 ribonucleotides in length, e.g., X1 or X2 are 1, 2, 3, 4, 5, 6, 7, 8, 9, 10, or 15 ribonucleotides in length, as well as the corresponding DNA sequences, and sequences having at least 90%, 92%, 95%, 96%, or 99% identity thereto. In one embodiment, the ribonucleotides or deoxyribonucleotides include one or more modified ribonucleotides or deoxyribonucleotides, e.g., modified phosphate linkages, modified sugars, modified nucleobases, or combinations thereof.

In one embodiment, miRNAs useful in the methods include but are not limited to 5'X1AAGGX3UAX23' (SEQ ID NO:7), wherein X3 is not c, and X1 and X2 are independently absent or are from 1 to 20 ribonucleotides in length, e.g., X1 or X2 are 1, 2, 3, 4, 5, 6, 7, 8, 9, 10, or 15 ribonucleotides in length, as well as the corresponding miRNA DNA sequences, and sequences having at least 90%, 92%, 95%, 96%, or 99% identity thereto. In one embodiment, the ribonucleotides or deoxyribonucleotides include one or more modified ribonucleotides or deoxyribonucleotides, e.g., modified phosphate linkages, modified sugars, modified nucleobases, or combinations thereof.

In one embodiment, miRNAs useful in the methods include but are not limited to 5'X1AAGGCXAX23' (SEQ ID NO:8), wherein X3 is not u, and X1 and X2 are independently absent or are from 1 to 20 ribonucleotides in length, e.g., X1 or X2 are 1, 2, 3, 4, 5, 6, 7, 8, 9, 10, or 15 ribonucleotides in length, as well as the corresponding DNA sequences, and sequences having at least 90%, 92%, 95%, 96%, or 99% identity thereto. In one embodiment, the ribonucleotides or deoxyribonucleotides include one or more modified ribonucleotides or deoxyribonucleotides, e.g., modified phosphate linkages, modified sugars, modified nucleobases, or combinations thereof.

In one embodiment, miRNAs useful in the methods include but are not limited to 5'X1AAGGCUX3X23' (SEQ ID NO:9), wherein X3 is not a, and X1 and X2 are independently absent or are from 1 to 20 ribonucleotides in length, e.g., X1 or X2 are 1, 2, 3, 4, 5, 6, 7, 8, 9, 10, or 15 ribonucleotides in length, as well as the corresponding m DNA sequences. In one embodiment, the ribonucleotides or deoxyribonucleotides include one or more modified ribonucleotides or deoxyribonucleotides, e.g., modified phosphate linkages, modified sugars, modified nucleobases, or combinations thereof.

In one embodiment, the delivery of the miRNA is in the form of a double-stranded or triple stranded molecule. For example, the antisense sequence (passenger strand) of any of the molecules described above may be employed to form a double stranded molecule, e.g., in a hairpin-loop structure or two separate strands. In one embodiment, the modifications in ribonucleotides or deoxyribonucleotide are in the antisense strand. In one embodiment, the modifications in the modified ribonucleotides or deoxyribonucleotide are in the sense strand. In one embodiment, the modifications are not in the seed region. In one embodiment, a modification is a LNA. In one embodiment, the modification includes one or more phosphorothioate groups, modification at 2-hydroxyl groups in sugar, modifications that enhance stability, e.g., decrease degradation rates of the sense strand, or decrease stability, e.g., of the antisense strand after it is dissociated from the sense strand. In one embodiment, the antisense strand may be chemically coupled to a molecule that enhances uptake, e.g., associated with or chemically coupled to cholesterol or a lipid.

The nucleic acid molecules, sense or antisense, may be of any length. In one embodiment, the sense nucleic acid molecule may be from 6 to 100 nucleotides in length, e.g., from 6 to 22, 6 to 25, 6 to 30, 20 to 30, 30 to 40, or 50 to 100 nucleotides in length. In one embodiment, the antisense nucleic acid molecule may be from 6 to 100 nucleotides in length, e.g., from 6 to 22, 6 to 25, 6 to 30, 20 to 30, 30 to 40, or 50 to 100 nucleotides in length. In one embodiment, the sense nucleic acid molecule is shorter than the antisense nucleic acid molecule. In one embodiment, for single stranded nucleic acid molecules that form hairpin-loops, the nucleic acid molecule may be from 14 to 200 nucleotides in length, e.g., from 14 to 25, 14 to 30, 20 to 40, 50 to 100, or 100 to 200 nucleotides in length.

Delivery Vehicles

Delivery vehicles for the miRNA-690 or DNA therefore in the compositions include, for example, naturally occurring polymers, microparticles, nanoparticles, and other macromolecular complexes capable of mediating delivery of a nucleic acid to a host cell. Vehicles can also comprise other components or functionalities that further modulate, or that otherwise provide beneficial properties.

In one embodiment, the delivery vehicle is a naturally occurring polymer, e.g., formed of materials including but not limited to albumin, collagen, fibrin, alginate, extracellular matrix (ECM), e.g., xenogeneic ECM, hyaluronan (hyaluronic acid), chitosan, gelatin, keratin, potato starch hydrolyzed for use in electrophoresis, or agar-agar (agarose). In one embodiment, the delivery vehicle comprises a hydrogel. In one embodiment, the composition comprises a naturally occurring polymer. For example, the miRNA may be in nanoparticles or microparticles. Table 1 provides exemplary materials for delivery vehicles that are formed of naturally occurring polymers and materials for particles.

TABLE 1

| Particle class | Materials |
| --- | --- |
| Natural materials or derivatives | Chitosan |
| | Dextran |
| | Gelatine |
| | Albumin |
| | Alginates |
| | Liposomes |
| | Starch |
| Polymer carriers | Polylactic acid |
| | Poly(cyano)acrylates |
| | Polyethyleneimine |
| | Block copolymers |
| | Polycaprolactone |

An exemplary polycaprolactone is methoxy poly(ethylene glycol)/poly(epsilon caprolactone). An exemplary poly lactic acid is poly(D,L-lactic-co-glycolic)acid (PLGA).

Some examples of materials for particle formation include but are not limited to agar acrylic polymers, polyacrylic acid, poly acryl methacrylate, gelatin, polylactic acid), pectin(poly glycolic acid), cellulose derivatives, cellulose acetate phthalate, nitrate, ethyl cellulose, hydroxyl ethyl cellulose, hydroxypropylcellulose, hydroxyl propyl methyl cellulose, hydroxypropylmethylcellulose phthalate, methyl cellulose, sodium carboxymethylcellulose, poly(ortho esters), polyurethanes, poly(ethylene glycol), poly(ethylene vinyl acetate), polydimethylsiloxane, polyvinyl acetate phthalate), polyvinyl alcohol, polyvinyl pyrrolidone, and shellac. Soluble starch and its derivatives for particle preparation include amylodextrin, amylopectin and carboxy methyl starch.

In one embodiment, the polymers in the nanoparticles or microparticles are biodegradable. Examples of biodegradable polymers useful in particles preparation include synthetic polymers, e.g., polyesters, poly(ortho esters), polyanhydrides, or polyphosphazenes; natural polymers including proteins (e.g., collagen, gelatin, and albumin), or polysaccharides (e.g., starch, dextran, hyaluronic acid, and chitosan). For instance, a biocompatible polymer includes poly (lactic) acid (PLA), poly (glycolic acid) (PLGA). Natural polymers that may be employed in particles (or as the delivery vehicle) include but are not limited to albumin, chitin, starch, collagen, chitosan, dextrin, gelatin, hyaluronic acid, dextran, fibrinogen, alginic acid, casein, fibrin, and polyanhydrides.

In one embodiment, the delivery vehicle is a hydrogel. Hydrogels can be classified as those with chemically crosslinked networks having permanent junctions or those with physical networks having transient junctions arising from polymer chain entanglements or physical interactions, e.g., ionic interactions, hydrogen bonds or hydrophobic interactions. Natural materials useful in hydrogels include natural polymers, which are biocompatible, biodegradable, support cellular activities, and include proteins like fibrin, collagen and gelatin, and polysaccharides like starch, alginate and agarose.

In one embodiment, a non-viral delivery vehicle comprises inorganic nanoparticles, e.g., calcium phosphate or silica particles; polymers including but not limited to poly (lactic-co-glycolic acid) (PLGA), polylactic acid (PLA), linear and/or branched PEI with differing molecular weights (e.g., 2, 22 and 25 kDa), dendrimers such as polyamidoamine (PAMAM) and polymethoacrylates; lipids including but not limited to cationic liposomes, cationic emulsions, DOTAP, DOTMA, DMRIE, DOSPA, distearoylphosphatidylcholine (DSPC), DOPE, or DC-cholesterol; peptide based vectors including but not limited to Poly-L-lysine or protamine; or poly(β-amino ester), chitosan, PEI-polyethylene glycol, PEI-mannose-dextrose, DOTAP-cholesterol or RNAiMAX.

Viral vectors for delivery are also envisioned, e.g., retrovirus lentivirus, adenovirus, herpesvirus or adeno-associated virus vectors.

In one embodiment, the delivery vehicle is a glycopolymer-based delivery vehicle, poly(glycoamidoamine)s (PGAAs), that have the ability to complex with various polynucleotide types and form nanoparticles. These materials are created by polymerizing the methylester or lactone derivatives of various carbohydrates (D-glucarate (D), meso-galactarate (G), D-mannarate (M), and L-tartarate (T)) with a series of oligoethyleneamine monomers (containing between 1-4 ethylenamines. A subset composed of these carbohydrates and four ethyleneamines in the polymer repeat units yielded exceptional delivery efficiency.

In one embodiment, the delivery vehicle comprises polyethyleneimine (PEI), polyamidoamine (PAMAM), PEI-PEG, PEI-PEG-mannose, dextran-PEI, OVA conjugate, PLGA microparticles, or PLGA microparticles coated with PAMAM.

In one embodiment, the delivery vehicle comprises a cationic lipid, e.g., N-[1-(2,3-dioleoyloxy)propel]-N,N,N-trimethylammonium (DOTMA), 2,3-dioleyloxy-N-[2-spermine carboxamide] ethyl-N,N-dimethyl-1-propanammonium trifluoroacetate (DOSPA, Lipofectamine); 1,2-dioleoyl-3-trimethylammonium-propane (DOTAP); N-[1-(2,3-dimyristloxy) propyl]; N,N-dimethyl-N-(2-hydroxyethyl) ammonium bromide (DMRIE), 3-β-[N-(N,N'-dimethylaminoethane) carbamoyl] cholesterol (DC-Chol); dioctadecyl amidoglyceryl spermine (DOGS, Transfectam); or imethyl-dioctadeclyammonium bromide (DDAB). The positively charged hydrophilic head group of cationic lipids usually consists of monoamine such as tertiary and quaternary amines, polyamine, amidinium, or guanidinium group. A series of pyridinium lipids have been developed. In addition to pyridinium cationic lipids, other types of heterocyclic head group include imidazole, piperizine and amino acid. The main function of cationic head groups is to condense negatively charged nucleic acids by means of electrostatic interaction to slightly positively charged nanoparticles, leading to enhanced cellular uptake and endosomal escape.

Lipids having two linear fatty acid chains, such as DOTMA, DOTAP and SAINT-2, or DODAC, may be employed as a delivery vehicle, as well as tetraalkyl lipid chain surfactant, the dimer of N,N-dioleyl-N,N-dimethyl-ammonium chloride (DODAC). All the trans-orientated lipids regardless of their hydrophobic chain lengths ($C_{16:1}$, $C_{18:1}$ and $C_{20:1}$) appear to enhance the transfection efficiency compared with their cis-orientated counterparts.

The structures of cationic polymers useful as a delivery vehicle include but are not limited to linear polymers such as chitosan and linear poly(ethyleneimine), branched polymers such as branch poly(ethyleneimine) (PEI), circle-like polymers such as cyclodextrin, network (crosslinked) type polymers such as crosslinked poly(amino acid) (PAA), and dendrimers. Dendrimers consist of a central core molecule, from which several highly branched arms 'grow' to form a tree-like structure with a manner of symmetry or asymmetry. Examples of dendrimers include polyamidoamine (PAMAM) and polypropylenimine (PPI) dendrimers.

DOPE and cholesterol are commonly used neutral co-lipids for preparing cationic liposomes. Branched PEI-cholesterol water-soluble lipopolymer conjugates self-assemble into cationic micelles. Pluronic (poloxamer), a non-ionic polymer and SP1017, which is the combination of Pluronics L61 and F127, may also be used.

In one embodiment, PLGA particles are employed to increase the encapsulation frequency although complex formation with PLL may also increase the encapsulation efficiency. Other cationic materials, for example, PEI, DOTMA, DC-Chol, or CTAB, may be used to make nanospheres.

In one embodiment, no delivery vehicle is employed, e.g., naked RNA is employed alone or with a scaffold.

In one embodiment, physical methods including but not limited to electroporation, sonoporation, magnetoporation, ultrasound or needle injection may be employed to introduce naked miRNA, complexes of miRNA and a delivery vehicle or miRNA encapsulated in particles.

Routes, Formulations and Dosages

The disclosed nucleic acid molecules can be formulated as pharmaceutical compositions and administered to a mammalian host, such as a human patient in a variety of forms adapted to the chosen route of administration, e.g., orally or parenterally, by intravenous, intramuscular, topical, local, or subcutaneous routes. The composition having is administered therapeutically or is administered prophylactically.

In one embodiment, the disclosed nucleic acid molecules may be administered by infusion or injection. Solutions of the miRNA or its salts, can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion may include sterile aqueous solutions or dispersions or sterile powders comprising the active ingredient which are adapted for the extemporaneous preparation of sterile injectable or infusible solutions or dispersions, optionally encapsulated in complexes, liposomes, nanoparticles or microparticles. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In some cases, it may be preferable to include isotonic agents, for example, sugars, buffers or sodium chloride. Prolonged absorption of the injectable compositions can be brought about by the use in the compositions of agents delaying absorption, for example, microparticles, or aluminum monostearate and gelatin.

Sterile injectable solutions are prepared by incorporating the active agent in the required amount in the appropriate solvent with various of the other ingredients enumerated above, as required, followed by filter sterilization. In the case of sterile powders For the preparation of sterile injectable solutions, the methods of preparation include vacuum drying and the freeze drying techniques, which yield a powder of the active ingredient plus any additional desired ingredient present in the previously sterile-filtered solutions.

Useful solid carriers may include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as antimicrobial agents can be added to optimize the properties for a given use. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Useful dosages of the miRNA-690 can be determined by comparing their in vitro activity and in vivo activity in animal models thereof. Methods for the extrapolation of effective dosages in mice, and other animals, to humans are known to the art.

Generally, the concentration of the miRNA in a liquid composition, may be from about 0.1-25 wt-%, e.g., from about 0.5-10 wt-%. The concentration in a semi-solid or solid composition such as a gel or a powder may be about 0.1-5 wt-%, e.g., about 0.5-2.5 wt-%.

The amount of the miRNAs for use alone or with other agents will vary with the route of administration, the nature of the condition being treated and the age and condition of the patient and will be ultimately at the discretion of the attendant physician or clinician.

The miRNA may be conveniently administered in unit dosage form; for example, containing 5 to 1000 mg, conveniently 10 to 750 mg, or conveniently 50 to 500 mg of active ingredient per unit dosage form.

In general, a suitable dose may be in the range of from about 0.5 to about 100 mg/kg, e.g., from about 10 to about 75 mg/kg of body weight per day, such as 3 to about 50 mg per kilogram body weight of the recipient per day, for example in the range of 6 to 90 mg/kg/day, e.g., in the range of 15 to 60 mg/kg/day.

Exemplary Delivery Vehicles

The isolated miRNA-690 nucleic acid described herein may be delivered by any of a variety of vehicles including but not limited to viruses, liposomes or other nanoparticles. The nucleic acid may form complexes with one or more non-nucleic acid molecules or may be encapsulated in or on the surface of delivery vehicles such as nanoparticles one embodiment, the miRNA has at least 70%, 80%, e.g., at least 85%, 87%, 90%, 92%, 93%, 94%, 95%, 96%, 97%, 98% or 99% nucleic acid sequence identity to 5'-AAAGGCUAGG-CUCACAACCAAA-3' (SEQ ID NO:1).

Numerous lipids which are used in liposome delivery systems may be used to form a lipid layer, e.g., a bi-layer. Exemplary lipids for use include, for example, 1,2-dioleoyl-sn-glycero-3-phosphocholine (DOPC), 1,2-dipalmitoyl-sn-glycero-3-phosphocholine (DPPC), 1,2-distearoyl-sn-glyc-ero-3-phosphocholine (DSPC), 1,2-dioleoyl-sn-glycero-3-[phosphor-L-serine] (DOPS), 1,2-dioleoyl-3-trimethylammonium-propane (18:1 DOTAP), 1,2-dioleoyl-sn-glycero-3-phospho-(1'-rac-glycerol) (DOPG), 1,2-dioleoyl-sn-glycero-3-phosphoethanolamine (DOPE), 1,2-dipalmitoyl-sn-glycero-3-phosphoethanolamine (DPPE), 1,2-dioleoyl-sn-glycero-3-phosphoethanolamine-N-[methoxy(polyethylene glycol)-2000] (18:1 PEG-2000 PE), 1,2-dipalmitoyl-sn-glycero-3-phosphoethanolamine-N-[methoxy(polyethylene glycol)-2000] (16:0 PEG-2000 PE), 1-oleoyl-2-[12-[(7-nitro-2-1,3-benzoxadiazol-4-yl)amino] lauroyl]-sn-glycero-3-phosphocholine (18:1-12:0 NBD PC), 1-palmitoyl-2-{12-[(7-nitro-2-1,3-benzoxadiazol-4-yl) amino]lauroyl}-sn-glycero-3-phosphocholine (16:0-12:0 NBD PC), cholesterol and mixtures/combinations thereof. Cholesterol, not technically a lipid, but presented as a lipid for purposes of an embodiment. Often cholesterol is incorporated into lipid bi-layers to enhance structural integrity of the bi-layer.

In one embodiment, anionic liposomal particles are employed as a delivery vehicle for the nucleic acid molecules, wherein the anionic liposomal particles optionally comprise one or more targeting moieties. In one embodiment, the anionic liposomal nanoparticles have diameters of about 100 nm to about 500 nm. In one embodiment, the anionic liposomal nanoparticles have diameters of about 150 nm to about 250 nm. In one embodiment, the lipid layer comprises lipids including but not limited to 1,2-dioleoyl-sn-glycero-3-phosphocholine (DOPC), 1,2-dipalmitoyl-sn-glycero-3-phosphocholine (DPPC), 1,2-distearoyl-sn-glyc-ero-3-phosphocholine (DSPC), 1,2-dioleoyl-sn-glycero-3-[phosphor-L-serine] (DOPS), 1,2-dioleoyl-3-trimethylammonium-propane (18:1 DOTAP), 1,2-dioleoyl-sn-glycero-3-phospho-(1'-rac-glycerol) (DOPG), 1,2-dioleoyl-sn-glycero-3-phosphoethanolamine (DOPE), 1,2-dipalmitoyl-sn-glycero-3-phosphoethanolamine (DPPE), 1,2-dioleoyl-sn-glycero-3-phosphoethanolamine-N-[methoxy(polyethylene glycol)-2000] (18:1 PEG-2000 PE), 1,2-dipalmitoyl-sn-glycero-3-phosphoethanolamine-N-[methoxy(polyethylene glycol)-2000] (16:0 PEG-2000 PE), 1-oleoyl-2-[12-[(7-nitro-2-1,3-benzoxadiazol-4-yl)amino] lauroyl]-sn-glycero-3-phosphocholine (18:1-12:0 NBD PC), 1-palmitoyl-2-{12-[(7-nitro-2-1,3-benzoxadiazol-4-yl) amino]lauroyl}-sn-glycero-3-phosphocholine (16:0-12:0 NBD PC), and mixtures thereof; or wherein said lipid layer comprises 1,2-distearoyl-sn-glycero-3-phosphocholine (DSPC), 1,2-dioleoyl-sn-glycero-3-phosphoethanolamine (DOPE), or a mixture thereof; or wherein said lipid layer comprises cholesterol. In one embodiment, the lipid layer comprises two or more of DPPC, DMPG or cholesterol.

In certain embodiments, liposomes generally range in size from about 8 to 10 nm to about 5 μm in diameter, e.g., about 20-nm to 3 μm in diameter, about 10 nm to about 500 nm, about 20-200-nm (including about 150 nm, which may be a mean or median diameter), about 50 nm to about 150 nm, about 75 to about 130 nm, or about 75 to about 100 nm as well as about 200 to about 450 nm, about 100 to about 200 nm, about 150 to about 250 nm, or about 200 to about 300 nm.

In certain embodiments, the delivery vehicle may be a biodegradable polymer comprising one or more aliphatic polyesters, poly (lactic acid) (PLA), poly (glycolic acid) (PGA), co-polymers of lactic acid and glycolic acid (PLGA), polycaprolactone (PCL), polyanhydrides, poly(or-tho)esters, polyurethanes, poly(butyric acid), poly(valeric acid), poly(lactide-co-caprolactone), alginate and other polysaccharides, collagen, and chemical derivatives thereof, albumin a hydrophilic protein, zein, a prolamine, a hydro-phobic protein, and copolymers and mixtures thereof.

In other embodiments, the lipid bi-layer is comprised of a mixture of DSPC, DOPC and optionally one or more phosphatidyl-cholines (PCs) selected from the group consisting of 1,2-dimyristoyl-sn-glycero-3-phosphocholine (DMPC), 1,2-dioleoyl-3-trimethylammonium-propane (DOTAP), 1-palmitoyl-2-oleoyl-sn-glycero-3-phosphocho-line (POPC), a lipid mixture comprising (in molar percent) between about 50% to about 70% or about 51% to about 69%, or about 52% to about 68%, or about 53% to about 67%, or about 54% to about 66%, or about 55% to about 65%, or about 56% to about 64%, or about 57% to about 63%, or about 58% to about 62%, or about 59% to about 61%, or about 60%, of one or more unsaturated phosphati-dyl-choline, DMPC [14:0] having a carbon length of 14 and no unsaturated bonds, 1,2-dipalmitoyl-sn-glycero-3-phos-phocholine (DPPC) [16:0], POPC [16:0-18:1] and DOTAP [18:1]; and wherein (b) the molar concentration of DSPC and DOPC in the mixture is between about 10% to about 99% or about 50% to about 99%, or about 12% to about 98%, or about 13% to about 97%, or about 14% to about 96%, or about 55% to about 95%, or about 56% to about 94%, or about 57% to about 93%, or about 58% to about 42%, or about 59% to about 91%, or about 50% to about 90%, or about 51% to about 89%.

In certain embodiments, the lipid bi-layer is comprised of one or more compositions selected from the group consisting of a phospholipid, a phosphatidyl-choline, a phosphatidyl-serine, a phosphatidyl-diethanolamine, a phosphatidylinosite, a sphingolipid, and an ethoxylated sterol, or mixtures thereof. In illustrative examples of such embodiments, the phospholipid can be a lecithin; the phosphatidylinosite can be derived from soy, rape, cotton seed, egg and mixtures thereof; the sphingolipid can be ceramide, a cerebroside, a sphingosine, and a sphingomyelin, and a mixture thereof; the ethoxylated sterol can be phytosterol, PEG-(polyethyleneglycol)-5-soy bean sterol, and PEG-(polyethyleneglycol)-5 rapeseed sterol. In certain embodiments, the phytosterol comprises a mixture of at least two of the following compositions: sitosterol, campesterol and stig-masterol.

In still other illustrative embodiments, the lipid bi-layer is comprised of one or more phosphatidyl groups selected from the group consisting of phosphatidyl choline, phosphatidyl-ethanolamine, phosphatidyl-serine, phosphatidyl-inositol, lyso-phosphatidyl-choline, lyso-phosphatidyl-etha-nolamine, lyso-phosphatidyl-inositol and lyso-phosphati-dyl-inositol.

In still other illustrative embodiments, the lipid bi-layer is comprised of phospholipid selected from a monoacyl or diacylphosphoglyceride.

In still other illustrative embodiments, the lipid bi-layer is comprised of one or more phosphoinositides selected from the group consisting of phosphatidyl-inositol-3-phosphate (PI-3-P), phosphatidyl-inositol-4-phosphate (PI-4-P), phos-phatidyl-inositol-5-phosphate (PI-5-P), phosphatidyl-inosi-tol-3,4-diphosphate (PI-3,4-P2), phosphatidyl-inositol-3,5-diphosphate (PI-3,5-P2), phosphatidyl-inositol-4,5-diphosphate (PI-4,5-P2), phosphatidyl-inositol-3,4,5-triphosphate (PI-3,4,5-P3), lysophosphatidyl-inositol-3-phosphate (LPI-3-P), lysophosphatidyl-inositol-4-phosphate (LPI-4-P), lysophosphatidyl-inositol-5-phosphate (LPI-5-P), lysophosphatidyl-inositol-3,4-diphosphate (LPI-3,4-P2), lysophosphatidyl-inositol-3,5-diphosphate (LPI-3,5-P2), lysophosphatidyl-inositol-4,5-diphosphate (LPI-4,5-P2), and lysophosphatidyl-inositol-3,4,5-diphosphate (LPI-3,4,5-P3), and phosphatidyl-inositol (PI), and lysophosphatidyl-inositol (LPI).

In still other illustrative embodiments, the lipid bi-layer is comprised of one or more phospholipids selected from the group consisting of PEG-poly(ethylene glycol)-derivatized distearoylphosphatidylethanolamine (PEG-DSPE), PEG-poly(ethylene glycol)-derivatized dioleoylphosphatidyletha-nolamine (PEG-DOPE), poly(ethylene glycol)-derivatized ceramides (PEG-CER), hydrogenated soy phosphatidylcho-line (HSPC), egg phosphatidylcholine (EPC), phosphatidyl ethanolamine (PE), phosphatidyl glycerol (PG), phosphatidyl inositol (PI), monosialoganglioside, sphingomyelin (SPM), distearoylphosphatidylcholine (DSPC), dimyris-toylphosphatidylcholine (DMPC), and dimyristoylphospha-tidylglycerol (DMPG).

In still other embodiments, the lipid bi-layer comprises one or more PEG-containing phospholipids, for example 1,2-dioleoyl-sn-glycero-3-phosphoethanolamine-N-[methoxy(polyethylene glycol)] (ammonium salt) (DOPE-PEG), 1,2-distearoyl-sn-glycero-3-phosphoethanolamine-N-[methoxy(polyethylene glycol)] (ammonium salt) (DSPE-PEG), 1,2-distearoyl-sn-glycero-3-phosphoetha-nolamine-N-[amino(polyethylene glycol)] (DSPE-PEG-NH$_2$) (DSPE-PEG). In the PEG-containing phospholipid, the PEG group ranges from about 2 to about 250 ethylene glycol units, about 5 to about 100, about 10 to 75, or about 40-50 ethylene glycol units. In certain exemplary embodi-ments, the PEG-phospholipid is 1,2-dioleoyl-sn-glycero-3-phosphoethanolamine-N-[methoxy(polyethylene glycol)-2000] (ammonium salt) (DOPE-PEG$_{2000}$), 1,2-distearoyl-sn-glycero-3-phosphoethanolamine-N-[methoxy (polyethylene glycol)-2000] (ammonium salt) (DSPE-PEG$_{2000}$), 1,2-distearoyl-sn-glycero-3-phosphoethanolamine-N-[amino(polyethylene glycol)-2000] (DSPE-PEG$_{2000}$-NH$_2$) which can be used to covalent bind a functional moiety to the lipid bi-layer.

In certain embodiments, the lipid bi-layer is comprised of one or more phosphatidylcholines (PCs) selected from the group consisting of 1,2-distearoyl-sn-glycero-3-phospho-choline (DSPC) [18:0], 1,2-dioleoyl-sn-glycero-3-phospho-choline (DOPC) [18:1 (Δ9-Cis)], 1,2-dimyristoyl-sn-glyc-ero-3-phosphocholine (MPG), 1,2-dioleoyl-3-trimethylammonium-propane (DOTAP), 1-palmitoyl-2-oleoyl-sn-glycero-3-phosphocholine (POPC), egg PC, and a lipid mixture comprising of one or more unsaturated phos-phatidyl-cholines, DMPC [14:0] having a carbon length of 14 and no unsaturated bonds, 1,2-dipalmitoyl-sn-glycero-3-phosphocholine (DPPC) [16:0], POPC [16:0-18:1], and DOTAP [18:1]. The use of DSPC and/or DOPC as well as other zwitterionic phospholipids as a principal component (often in combination with a minor amount of cholesterol) is employed in certain embodiments in order to provide a protocell with a surface zeta potential which is neutral or close to neutral in character.

Cationic liposomes may be formed from a single type of lipid, or a combination of two or more distinct lipids. For instance, one combination may include a cationic lipid and a neutral lipid, or a cationic lipid and a non-cationic lipid. Exemplary lipids for use in the cationic liposomes include but are not limited to DOTAP, DODAP, DDAB, DOTMA, MVL5, DPPC, DSPC, DOPE, DPOC, POPC, or any com-bination thereof. In one embodiment, the cationic liposome has one or more of the following lipids or precursors thereof: N-[1-(2,3-dioleyloxy)propyl]-N,N,N-trimethylammonium chloride with a monovalent cationic head; N',N'-diocta-decyl-N-4,8-diaza-10-aminodecanoyl glycine amide; 1,4,7, 10-tetraazacyclododecane cyclen; imidazolium-containing cationic lipid having different hydrophobic regions (e.g., cholesterol and diosgenin); 1,2-dioleoyl-sn-glycero-3-phos-phoethanolamine (DOPE); 3β-[N-(N',N'-dimethylamino-ethane) carbamoyl) cholesterol (DC-Chol) and DOPE; O,O'-ditetradecanoyl-N-(α-trimethyl ammonioacetyl) diethanol-amine chloride, DOPE and cholesterol, phosphatidylcholine; 1,2-dilinoleyl-4-(2-dimethylamino-ethyl)-[1,3]-dioxolane, 1,2-distearoyl-sn-glycerol-3-phos-phocholine (DSPC) and cholesterol, 1-palmitoyl-2-oleoyl-sn-glycero-3-phosphocholine, DOPE, and 1,2-distearoyl-sn-glycero-3-phosphoethanolamine-N-(methoxy[polyethylene glycol-2000), 1,2-di-O-octadecenyl-3-trimethylammonium propane, cholesterol, and D-α-toco; 1,2-dioleoyl-3-trimeth-ylammonium-propane, cholesterol; 3-β(N-(N',N'-dimethyl, N'-hydroxyethyl amino-propane) carbamoyl) cholesterol iodide, DMHAPC-Chol and DOPE in equimolar proportion, or 1-palmitoyl-2-oleoyl-sn-glycero-3-ethylphosphocholine: cholesterol, dimethyldioctadecylammonium (DDAB); 1,2-di-O-octadecenyl-3-trimethylammonium propane;N1-[2-((1S)-1-{(3-aminopropyl)amino]-4-[di(3-amino-propyl) amino)amino]butylcarboxamido)ethyl]-3,4-di[oleyloxy]-benzamide (MVL5); 1,2-dioleoyl-3-dimethylammonium-propane (DODAP); 1,2-di-O-octadecenyl-3-trimethylammonium propane (DOTMA); 1,2-dioleoyl-sn-glycero-3-phosphocholine (DOPC);1-palmitoyl-2-oleoyl-sn-glycero-3-phosphocholine (POPC).

Exemplary Routes, Formulations and Dosages

Administration of compositions having one or more nucleic acid molecules disclosed herein, can be via any of suitable route of administration, particularly parenterally, for example, intravenously, intra-arterially, intraperitoneally, intrathecally, intraventricularly, intracranially, intramuscu-larly, or subcutaneously. Such administration may be as a single bolus injection, multiple injections, or as a short- or long-duration infusion. Implantable devices (e.g., implant-able infusion pumps) may also be employed for the periodic parenteral delivery over time of equivalent or varying dos-ages of the particular formulation. For such parenteral administration, the nucleic acid compounds may be formu-lated as a sterile solution in water or another suitable solvent or mixture of solvents. The solution may contain other substances such as salts, sugars (particularly glucose or mannitol), to make the solution isotonic with blood, buff-ering agents such as acetic, critric, and/or phosphoric acids and their sodium salts, and preservatives.

The compositions alone or in combination with other active agents can be formulated as pharmaceutical compo-sitions and administered to a mammalian host, such as a human patient in a variety of forms adapted to the chosen route of administration, e.g., orally or parenterally, by intra-venous, intramuscular, topical or subcutaneous routes.

Thus, the compositions alone or in combination with another active agent, may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incor-porated directly with the food of the patient's diet. For oral therapeutic administration, the composition having nucleic acid, optionally in combination with another active com-pound, may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of the nucleic acid and optionally other active compound in such useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the composition optionally in combination with another active compound may be incorporated into sustained-release preparations and devices.

The composition having nucleic acid optionally in combination with another active compound may also be administered intravenously or intraperitoneally by infusion or injection, Solutions of the nucleic acid molecule optionally in combination with another active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the nucleic acid which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of particle size in the case of dispersions or by the use of surfactants. The prevention of the action of microorganisms during storage can be brought about by various antibacterial and antifungal agents, for example, parabens, chlorobutanol, phenol, sorbic acid, thimerosal, and the like. In many cases, it may be useful to include isotonic agents, for example, sugars, buffers or sodium chloride. Prolonged absorption of the injectable compositions can be brought about by the use in the compositions of agents delaying absorption, for example, aluminum monostearate and gelatin, or a combination thereof.

For example, sterile injectable solutions are prepared by incorporating compound(s) in an effective amount in the appropriate solvent with various of the other ingredients enumerated above, followed by filter sterilization. Generally, dispersions can be prepared by incorporating the selected sterilized active ingredient(s), e.g., via filer sterilization, into a sterile vehicle that contains the basic dispersion medium and any other optional ingredients from those enumerated above. The compositions disclosed herein may also be formulated in a neutral or salt form. Upon formulation, solutions will be administered in a manner compatible with the dosage formulation, and in such amount as is effective for the intended application. The formulations are readily administered in a variety of dosage forms such as injectable solutions, topical preparations, oral formulations, including sustain-release capsules, hydrogels, colloids, viscous gels, transdermal reagents, intranasal and inhalation formulations, and the like. For administration of an injectable aqueous solution, without limitation, the solution may be suitably buffered, if necessary, and the liquid diluent first rendered isotonic with sufficient saline or glucose. These particular aqueous solutions are especially suitable for intravenous; intramuscular, subcutaneous; transdermal, subdermal, and/or intraperitoneal administration. In this regard, the compositions of the present disclosure may be formulated in one or more pharmaceutically acceptable vehicles, including for example sterile aqueous media, buffers, diluents; and the like. For example, a given dosage of active ingredient(s) may be dissolved in a particular volume of an isotonic solution (e.g., an isotonic NaCl-based solution), and then injected at the proposed site of administration, or further diluted in a vehicle suitable for intravenous infusion (see, e.g., "REMINGTON'S PHARMACEUTICAL SCIENCES" $15^{th}$ Ed., pp. 1035-1038 and 1570-1580). While some variation in dosage will necessarily occur depending on the condition of the subject being treated, the extent of the treatment, and the site of administration, the person responsible for administration will nevertheless be able to determine the correct dosing regimens appropriate for the individual subject using ordinary knowledge in the medical and pharmaceutical arts.

In the case of sterile powders for the preparation of sterile injectable solutions, one method of preparation includes vacuum drying and the freeze drying techniques, which yield a powder of the active ingredient plus any additional desired ingredient present in the previously sterile-filtered solutions.

For topical administration, the composition optionally in combination with another active compound may be applied in pure form, e.g., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and antimicrobial agents can be added to optimize the properties for a given use.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

In addition, in one embodiment, the invention provides various dosage formulations of the nucleic acid optionally in combination with another active compound, e.g., for inhalation delivery. For example, formulations may be designed for aerosol use in devices such as metered-dose inhalers, dry powder inhalers and nebulizers.

Useful dosages can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the nucleic acid optionally in combination with another active compound in a liquid, solid or gel composition, may be from about 0.1-25 wt-%, e.g., from about 0.5-10 wt-%, from 10 to 30 wt-%, 30 to 50 -wt%, 50 to 70-wt%, or about 70 to 90 wt-%. The concentration in a semi-solid or solid composition such as a gel or a powder may be about 0.1-5 wt-%, e.g., about 0.5-2.5 wt-% or about 0.5-10 wt-%, from 10 to 30 wt-%, 30 to 50-wt %, 50 to 70-wt %, or about 70 to 90 wt-%.

The active ingredient may be administered to achieve peak plasma concentrations of the active compound of from about 0.5 to about 75 $\mu$M, e.g., about 1 to 50 $\mu$M, such as about 2 to about 30 $\mu$M. This may be achieved, for example, by the intravenous injection of a 0.05 to 5% solution of the active ingredient, optionally in saline, or orally administered as a bolus containing about 1-100 mg of the active ingredient. Desirable blood levels may be maintained by continuous infusion to provide about 0.01-5.0 mg/kg/hr or by intermittent infusions containing about 0.4-15 mg/kg of the active ingredient(s).

The amount of the nucleic acid optionally in combination with another active compound, or an active salt or derivative thereof, for use in treatment will vary not only with the particular salt selected but also with the route of administration, the nature of the condition being treated and the age and condition of the patient and will be ultimately at the discretion of the attendant physician or clinician. In general, however, a suitable dose may be in the range of from about 0.5 to about 100 mg/kg, e.g., from about 10 to about 75 mg/kg of body weight per day, such as 3 to about 50 mg per kilogram body weight of the recipient per day, for instance in the range of 6 to 90 mg/kg/day, e.g., in the range of 15 to 60 mg/kg/day. In one embodiment, 1 mg/kg to 100 mg/kg, e.g., per day, is administered. In one embodiment, 1 mg/kg to 20 mg/kg, e.g., per day, is administered. In one embodiment, 20 mg/kg to 40 mg/kg, e.g., per day, is administered. In one embodiment, 40 mg/kg to 60 mg/kg, e.g., per day, is administered. In one embodiment, 60 mg/kg to 80 mg/kg, e.g., per day, is administered. In one embodiment, 80 mg/kg to 100 mg/kg, e.g., per day, is administered. The nucleic acid optionally in combination with another active compound may be conveniently administered in unit dosage form; for example, containing 5 to 1000 mg, conveniently 10 to 750 mg, most conveniently, 50 to 500 mg of active ingredient per unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye. The dose, and perhaps the dose frequency, will also vary according to the age, body weight, condition, and response of the individual patient. In general, the total daily dose range for an active agent for the conditions described herein, may be from about 50 mg to about 5000 mg, in single or divided doses. In one embodiment, a daily dose range should be about 100 mg to about 4000 mg, e.g., about 1000-3000 mg, in single or divided doses, e.g., 750 mg every 6 hr of orally administered compound. This may achieve plasma levels of about 500-750 uM, In managing the patient, the therapy may be initiated at a lower dose and increased depending on the patient's global response.

The amount, dosage regimen, formulation, and administration of nucleic acid disclosed herein will be within the purview of the ordinary-skilled artisan having benefit of the present teaching. It is likely, however, that the administration of a therapeutically-effective amount of the disclosed compositions may be achieved by multiple, or successive administrations, over relatively short or even relatively prolonged periods, as may be determined by the medical practitioner overseeing the administration of such compositions to the selected individual. However, a single administration, such as, without limitation, a single injection of a sufficient quantity of the delivered agent may provide the desired benefit to the patient for a period of time.

In certain embodiments, the present disclosure concerns formulation of one or more cationic particles, e.g., cationic liposomes, for administration to an animal. In one embodiment, a cationic liposome comprises two or more distinct lipids, one of the lipids is cationic, e.g., DOTAP is a cationic lipid, and at least one of the others is non-cationic, e.g., DPPC or DSPC. Ratios of the two or more distinct lipids can vary, for example, for two distinct lipids, the ratio of a non-cationic lipid, e.g., neutral lipid, to the cationic lipid may be x:1 wherein x>1, x=1 or x:1 where x<1. In one embodiment, x>1. The formulation of pharmaceutically acceptable excipients and carrier solutions is well known to those of ordinary skill in the art, as is the development of suitable dosing and treatment regimens for using the particular cationic particle compositions described herein in a variety of treatment regimens. In certain circumstances it will be desirable to deliver the disclosed compositions in suitably-formulated pharmaceutical vehicles by one or more standard delivery methods, including, without limitation, subcutaneously, parenterally, intravenously, intramuscularly, intrathecally, orally, intraperitoneally, transdermally, topically, by oral or nasal inhalation, or by direct injection to one or more cells, tissues, or organs within or about the body of an animal. The methods of administration may also include those modalities as described in U.S. Pat. Nos. 5,543,158; 5,641,515, and 5,399,363, each of which is specifically incorporated herein in its entirety by express reference thereto. Solutions of the active compounds as freebase or pharmacologically acceptable salts may be prepared in sterile water, and may be suitably mixed with one or more surfactants, such as hydroxypropylcellulose. Dispersions may also be prepared in glycerol, liquid polyethylene glycols, oils, or mixtures thereof. Under ordinary conditions of storage and use, these preparations contain a preservative to prevent the growth of microorganisms.

The invention will be further described by the following non-limiting examples.

Example 1

Methods

| Resources Table | | |
|---|---|---|
| REAGENT or RESOURCE | SOURCE | IDENTIFIER |
| Antibodies | | |
| Anti-TSG101 | ThermoFisher Scientific | Cat# MA1-23296 |
| Anti-CD63 | ABclonal | Cat# A5271 |
| Anti-syntenin 1 | ThermoFisher | Cat# PA5-28826 |
| Anti-GAPDH | Cell signaling technology | Cat# 2118S |
| Anti-Dicer | ThermoFisher | Cat# MA5-7595 |
| Anti-Phospho-AKT Ser473 | Cell signaling technology | Cat# 9271S |
| Anti-pan AKT | Cell signaling technology | Cat# 4691S |
| Chemicals, Peptides, and Recombinant Proteins | | |
| Live/Dead Fixable Aqua dead cell stain kit | ThermoFisher | Cat# L34966 |
| Novolin R regular human insulin used in ITTs | Novo-Nordisk | Cat# NDC 0169-1833-11 |
| Insulin used in glucose uptake and hepatic glucose production assays | Sigma-Aldrich | Cat# I9278 |
| Glucagon | Sigma-Aldrich | Cat# G2044-1MG |
| Dextrose | Hospira, Inc | Cat# 0409-6648-02 |
| 3H-glucose | Perkin Elmer | Cat# NET331C001MC |
| Collagenase II | Sigma-Aldrich | Cat# C2674 |
| Percoll | GE Healthcare Life Sciences | Cat# 17-0891-01 |
| TRIzol RNA isolation reagent | ThermoFisher Scientific | Cat# 15596026 |
| SuperSignal West Pico Chemiluminescent Substrate | ThermoFisher Scientific | Cat# 34077 |
| Halt Protease and Phosphatase Inhibitor Cocktail | ThermoFisher Scientific | Cat# 78440 |
| RIPA buffer (10×) | Cell Signaling Technology | Cat# 9806 |
| PKH26 | Sigma-Aldrich | Cat# PKH26GL-1KT |
| 60% high fat diet | Research Diets | Cat# D12492 |
| Collagenase H | Roche | Cat# 11249002001 |
| RBC lysis buffer | eBioscience | Cat# 00-4333-57 |
| High-capacity CDNA reverse transcription kit | ThermoFisher Scientific | Cat# 4368813 |
| iTaq SYBR Green supermix | Bio-Rad | Cat# 172-5125 |
| Exosome-depleted FBS | SBI | Cat# EXO-FBSHI-50A-1 |
| Invivofectamine | ThermoFisher Scientific | Cat# IVF3005 |
| Lipofectamine RNAiMAX reagent | ThermoFisher Scientific | Cat# 13778-075 |
| X-tremeGENE HP DNA transfection reagent | Roche | Cat# 6366236001 |
| TaqMan ™ microRNA reverse transcription kit | ThermoFisher Scientific | Cat#4366597 |
| TaqMan ™ universal master mix II | ThermoFisher Scientific | Cat#4440040 |
| Recombinant murine IL4 | Peprotech | Cat# 214-14 |
| Recombinant murine IL13 | Peprotech | Cat# 210-13 |
| Commercial Assays | | |
| Direct-zol microprep kit | Zymo research | Cat# R2060 |
| Quick-RNA microprep kit | Zymo research | Cat#R1051 |
| Glucose colorimetric assay kit | Cayman | Cat# 10009582 |
| Insulin ELISA kit | ALPCO | Cat# 80-INSHU-E01.1 |
| Dual-Glo ® Luciferase Assay System | Promega | E2920 |
| Akt(pS473) + total Akt ELISA kit | Abcam | Cat# ab126433 |
| TruSeq Stranded mRNA Library Prep Kit | Illumina | Cat# 20020594 |
| Experimental Models: Cell Lines | | |
| 3T3-L1 cell line | ATCC | CRL-11506 |
| HEK293 cell line | ATCC | CRL-11268 |
| Deposited Data | | |
| RNA seq data | GEO database | GSE149610 |
| Experimental Models: Organisms/Strains | | |
| Mouse: WT C57BL6/J | Jackson Laboratories | JAX: 000664 |
| Mouse: Dicer flox/flox | Jackson Laboratories | JAX: 006366 |
| Mouse: LysMcre | Jackson Laboratories | JAX: 004781 |

-continued

| Resources Table | | |
|---|---|---|
| REAGENT or RESOURCE | SOURCE | IDENTIFIER |
| Oligonucleotides | | |
| Actb forward | Integrated DNA Technologies | GGCTGTATTCCCCTCCATCG (SEQ ID NO: 2) |
| Actb reverse | Integrated DNA Technologies | CCAGTTGGTAACAATGCCATGT (SEQ ID NO: 3) |
| Nadk forward | Integrated DNA Technologies | TCATGGGGATGAGACCTGGAG (SEQ ID NO: 4) |
| Nadk reverse | Integrated DNA Technologies | ACAAGCACACTCTTGGGAGAC (SEQ ID NO: 5) |
| miR-690 RT-PCR primer | ThermoFisher Scientific | Assay ID: 001677 |
| U6 snRNA RT-PCR primer | ThermoFisher Scientific | Assay ID: 001973 |
| miR-223 RT-PCR primer | ThermoFisher Scientific | Assay ID: 007896_mat |
| miR-690 mimic | ThermoFisher Scientific | Cat# 4464066 |
| miRNA mimic negative control | ThermoFisher Scientific | Cat# 4464058 |
| Cy3-labeled miR-690 mimic | Horizon | Cat# CTM-591175 |
| Nadk 3'-UTR reporter plasmid | Genecopoeia | Cat# MmiT094456-MT06 |
| Software and Algorithms | | |
| Prism | Graphpad | https://www.graphpad.com/scientific-software/prism/ |
| FlowJo | FlowJo | |
| ImageJ | NIH | https://imagej.nih.gov/ij/ |

Experimental Model and Subject Details

Mice

C57BL/6 (B6) mice were fed a high-fat diet (60% fat calories, 20% protein calories, and 20% carbohydrate calories; Research Diets) or a normal chow diet ad libitum. In most assays, the mice were fed with HFD for 12-16 weeks. B6 WT, Dicer flox/flox and LysMCre mice were purchased from the Jackson Laboratory. To generate myeloid cell-specific Dicer null mice, Dicer flox/flox were bred with transgenic mice harboring Cre recombinase driven by myeloid-specific lysozyme M promoter to create the following genotypes: Dicer flox/flox (control) and LysMCre-Dicer (DicerKO). All mice were maintained on a 12/12-hour light-dark cycle.

Study Approval

All animal procedures were done in accordance with University of California, San Diego Research Guidelines for the Care and Use of Laboratory Animals and all animals were randomly assigned to cohorts when used.

Differentiation of Adipocytes

To generate adipocytes, 3T3-L1 cells were differentiated in the induction medium (DMEM/F12 medium containing 4.5 g/L glucose, 10% FBS, penicillin-streptomycin, and glutamine and then induced with a differentiation cocktail consisting of 0.5 mM 3-isobutyl-1-methylxanthine, 1 μM dexamethasone, 10 μg/mL insulin, 0.2 mM indomethacin, and 1 μM rosiglitazone in DMEM supplemented with 10% FBS, PS, and glutamine) for 7-10 days.

Isolation of Primary Hepatocytes

Primary hepatocytes were isolated as described previously (Li et al., 2016; Ying et al., 2017). Briefly, mice were infused with a calcium free HEPES-phosphate buffer A (Calcium and magnesium-free PBS containing 0.2 μM EGTA, 10 mM HEPES, 1 mM glucose and 0.2% BSA, pH 7.4) via the vena cava for 3-5 min. After the color of the liver changed to a beige or light brown color, collagenase-containing buffer B (PBS with 1 mM magnesium and 1 mM calcium, 0.2% BSA, and 30 mM HEPES, 0.5 mg/ml collagenase H) was perfused into liver. After the appearance of cracking on the surface of liver, perfusion was stopped immediately and the liver was excised into ice-cold buffer A.

Cells from digested livers were teased out, suspended in Buffer A, filtered through 100 μm cell strainer, and centrifuged at 60×g for 6 min at 4° C. The pellet was washed with Buffer B (no collagenase) twice and then mixed with Percoll (adjusted to physiological ionic strength with 10× PBS) to a final concentration of 36% and centrifuged at 100×g for 10 min, 4° C. After removing the supernatant, the hepatocyte pellet was washed once with Buffer B (without collagenase) and then cultured in Williams Medium E containing 10% FBS on collagen-coated plates (GIBCO, Life Technologies) and antibiotics. After overnight incubation (16 hr), culture medium was refreshed.

Method Details

Glucose Tolerance and Insulin Tolerance Tests

For glucose tolerance tests, mice received one dose of dextrose (1 g/kg body weight) via i.p. injection after 12 hr of fasting. To measure the glucose-stimulated insulin secretion, about 20 μL of plasma were collected after glucose injection for 10 min, For insulin tolerance tests, mice were fasted for 6 hr and then i.p. injected with insulin (0.35 units/kg body weight for HFD mice).

Hyperinsulinemic-Euglycemic Clamp Studies

To perform hyperinsulinemic-euglycemic clamp assays, mice were surgerized with jugular vein cannulation. Three to five days after recovery, 6-hour fasted mice were infused with D-[3-3H] glucose (Perkin Elmer) for 90 min. After tracer equilibration, blood sampling occurred, then glucose (50% dextrose) and tracer (5 μCi/h) plus insulin (8 mU/kg/min) were infused into the jugular vein. Blood samples were measured from the tail vein at 10 min intervals. The steady-state conditions (120 mg/dl±10 mg/dl) was confirmed at the end of the clamp by maintaining a glucose infusion and plasma glucose concentration for a minimum of 20 min. Blood samples at time point=−10, 0 (basal), 110, and 120 (end of experiment) min were collected to determine glucose-specific activity, as well as free fatty acid and insulin concentration. Tracer-determined rates were quantified by using the Steele equation for steady-state conditions. At steady state, the rate of glucose disappearance (GDR) is equal to the sum of the rate of endogenous glucose productions (HGP) plus the exogenous GIR. The IS-GDR is equal to the total GDR minus the basal glucose turnover rate.

In vivo Insulin-Stimulated AKT Phosphorylation Assay

Tissue insulin action was evaluated by measuring insulin-stimulated AKT phosphorylation in liver, skeletal muscle, and epididymal white adipose (eWAT). Briefly, after 8 hr fasting, mice were anesthetized and parts of these insulin target tissues were collected to measure basal level of AKT phosphorylation. After a dose of insulin (0.35 U/kg body weight for HFD mice) injected via vena cava, parts of liver, skeletal muscle, and eWAT were collected at 3 min, 7 min, and 10 min, respectively. The phosphorylation of ATK was measured using AKT ELISA kits.

EV Purification and Characterization

The EVs from BMDM culture medium were prepared as previously described (Ying et al., 2017). After 24 hours culture, debris and dead cells in the medium were removed by centrifugation at 1,000×g for 10 min and then filtrated through a 0.2 μm filter. The medium was then subjected to ultracentrifugation at 100,000×g for 4 hours at 4° C. After wash with PBS (100,000×g for 20 min), the EV-containing pellet was resuspended 1 ml PBS and passed through a 0.2 μm filter to remove large particles. The particle size and concentration of ATM EVs were measured by NanoSight analysis (Malvern Instruments). To monitor EV trafficking, EVs were labeled with PKH26 fluorescent dye using the PKH26 fluorescent cell linker kit (Sigma-Aldrich). After PKH26 staining, the EVs were washed with PBS and collected by ultracentrifugation (100,000×g for 2 hours) at 4° C. Finally, PKH26 labeled EVs were resuspended in PBS.

In vivo EV Trafficking Assays

PKH26-labeled BMDM EVs or Cy3-miR-690 containing EVs ($1×10^9$ EVs per mouse) were delivered to HFD recipient mice through injection into tail vein. After 16 hours EV injection, parts of Liver, skeletal muscle, and eWAT were collected for detecting the appearance of PKH26 red fluorescence.

In Vivo and In Vitro EV Treatment

For in vitro assays, $1×10^8$ EVs on the basis of NanoSight analysis were added to $0.1×10^6$ cells for 36 hours. For in vivo treatment, recipient mice were intravenously injected $1×10^9$ EVs twice per week.

Differentiation of Bone Marrow-Derived Macrophages

Bone marrow-derived macrophages (BMDMs) were prepared as previously described (Ying et al., 2013). BMDMs were treated with IL4 (20 ng/mL) and IL13 (10 ng/mL) to stimulate M2 polarization. After 24 hours, culture medium was replaced and BMDMs were cultured for another 24 hours for exosome collection.

miR-690 Mimic Transfection or in vivo Treatment

Cy3 labeled miR-690 mimic or miR-690 mimic were transfected into recipient cells with the lipofectamine RNAiMAX reagent (ThermoFisher Scientific). After 24 hours, the transfection efficiencies were validated by qPCR analysis. For the in vivo delivery, miR-690 mimic was encapsulated with Invivofectamine and then administrated into obese/HFD recipient WT mice (5 nM mimic per mouse, twice per week) through tail vein injection.

Immuno-Fluorescence Staining

Parts of liver, skeletal muscle and eWAT of HFD mice were snap frozen in optimum cutting temperature (O.C.T., Fisher Healthcare) with dry ice. Six μm cryo-sections of tissue sections were cut and fixed with pre-cold acetone for 20 min. Immunostaining was performed as previously described. Slides were blocked with 5% normal donkey serum for 60 min at RT. After washing, nuclei were stained with DAPI (4',6-Diamidino-2-28 phenylindole dihydrochloride) for 10 min at room temperature. Mounting media and cover slips were then added to slides for imaging. Images were acquired on a Keyence Fluorescent Microscope, and were processed with ImageJ (NIH, Bethesda, MD).

Quantitative Reverse Transcriptase-Polymerase Chain Reaction (RT-PCR) Analysis

Total RNA was extracted from islet macrophages using the RNA extraction protocol according to the manufacturer's instructions (Zymo Research). cDNA was synthesized using Superscript III and random hexamers. qPCR was carried out in 10 μl reactions using iTaq SYBR Green supermix on a StepOnePlus Real-Time PCR Systems (ThermoFisher Scientific). For miRNA RT-PCR, cDNA was synthesized using TaqMan™ microRNA reverse transcription kit and miRNA primers (5x). qPCR was performed using TaqMan™ universal master mix II and miRNA primers (20x) in 10 μl reactions on a StepOnePlus Real-Time PCR Systems (ThermoFisher Scientific). The data presented correspond to the mean of $2^{-\Delta\Delta Ct}$ from at least three independent experiments after being normalized to β-actin or U6.

Glucose Uptake Assay

After 8 hr serum starvation, cells were stimulated with 100 nM insulin for 30 min in KRH buffer (137 nM NaCl, 4,8 mM KCl, 1.2 mM $KH_2PO_4$, 1.2 mM $MgSO_4$, 2.5 mM $CaCl_2$, 0.2% BSA, 16 mM HEPES) at 37'C. Then 3H-2-deoxy-D-glucose (3H-2-DOG, 0.1 mM, 0.4 μCi/ml) was supplemented to cells. After 10 min incubation at 37° C., cells were washed with ice-cold PBS twice. NaOH (1 N) was then added and incubated for 20 min to efficiently dissolve cells. An aliquot was used for protein concentration measurement. After neutralizing NaOH by adding HCl (1 N), the extracts were transferred to scintillation vials, and scintillation fluid was added and the radioactivity was counted. Results were normalized with protein concentration of cell lysates.

Glucose Output Assay

After 6 hr serum starvation, primary hepatocytes were washed twice and then exposed to glucose-free buffer (10 mM HEPES, 4 mM KCl, 125 mM NaCl, 0.85 mM $KH_2PO_4$, 1.25 mM $Na_2HPO_4$, 1 mM $CaCl_2$, and 15 mM $NaHCO_3$) containing glucagon (200 ng/ml), insulin (10 nM), or a combination of glucagon and insulin for 4 hours, at 37° C. Glucose production was determined by the measurement of glucose in the media. The primary hepatocytes attached the culture plate were dissolved by adding NaOH (1 N) and protein content was determined. The glucose results were normalized with protein concentration of cell lysates.

Western Blot Analysis

Cells or tissues were homogenized in RIPA buffer supplemented with protease and phosphatase inhibitors. Equal amounts of cell lysate proteins (30 μg protein per lane for pAKT detection) from each biological replicate were subjected to western blotting. Using ChemiDoc XRS imaging system (BioRad), the protein bands on blots were detected with the SuperSignal West Pico Chemiluminescent Substrate. Protein bands were analyzed using Image Lab software (BioRad). Western blot data in figures and supplemental figures are all representative of more than three independent experiments.

RNA-Seg Library Preparation and Sequencing

Total RNA was isolated from 3T3-L1 adipocytes treated with miR-690 mimic using the Zymo Direct-Zol MiniPrep kit. RNA purity was assessed by an Agilent 2100 Bioanalyzer. Sequencing libraries were prepared using a TruSeq Stranded mRNA Library Prep Kit (Illumina) according to the manufacturer's protocol. Samples were ligated to unique adaptors and subjected to PCR amplification. Libraries were then validated using an Agilent 2100 Bioanalyzer, normalized, and pooled for sequencing. RNA-seq libraries prepared from four biological replicates for each group as indicated were sequenced on an Illumina HiSeq 4000 using barcoded multiplexing. The RNA-seq data have been deposited in the NCBI Gene Expression Omnibus under accession number GSE149610.

miR-690 Target Gene Prediction and Validation miR-690 target gene prediction was conducted with TargetScan Mouse 7.2 (www.targetscan.org) (Agarwal et al., 2015). To validate that Nadk is a genuine target gene of miR-690, the luciferase reporter assay was carried out with 3' untranslated regions of Nadk containing potential WT or mutated miR-690 binding sites inserted downstream from the Renilla luciferase gene. The reporter constructs were cotransfected with miR-690 mimic or negative mimic control into HEK293 cells. After 24 hours cotransfection, the activities of Renilla luciferase were measured with the Dual-Glo luciferase reporter system.

Statistical Analysis

Tests used for statistical analyses are described in the figure legends. To assess whether the means of two groups are statistically different from each other, unpaired two-tailed Student's t test was used for statistical analyses using Prism8 software (GraphPad software v8.0; Prism, La Jolla, CA). P values of 0.05 or less were considered to be statistically significant. Degrees of significance were indicated in the figure legends. For the results of glucose and insulin tolerance tests, statistical comparisons between every two groups at each time point were performed with unpaired two-tailed Student's t test.

Results

Figure 8:
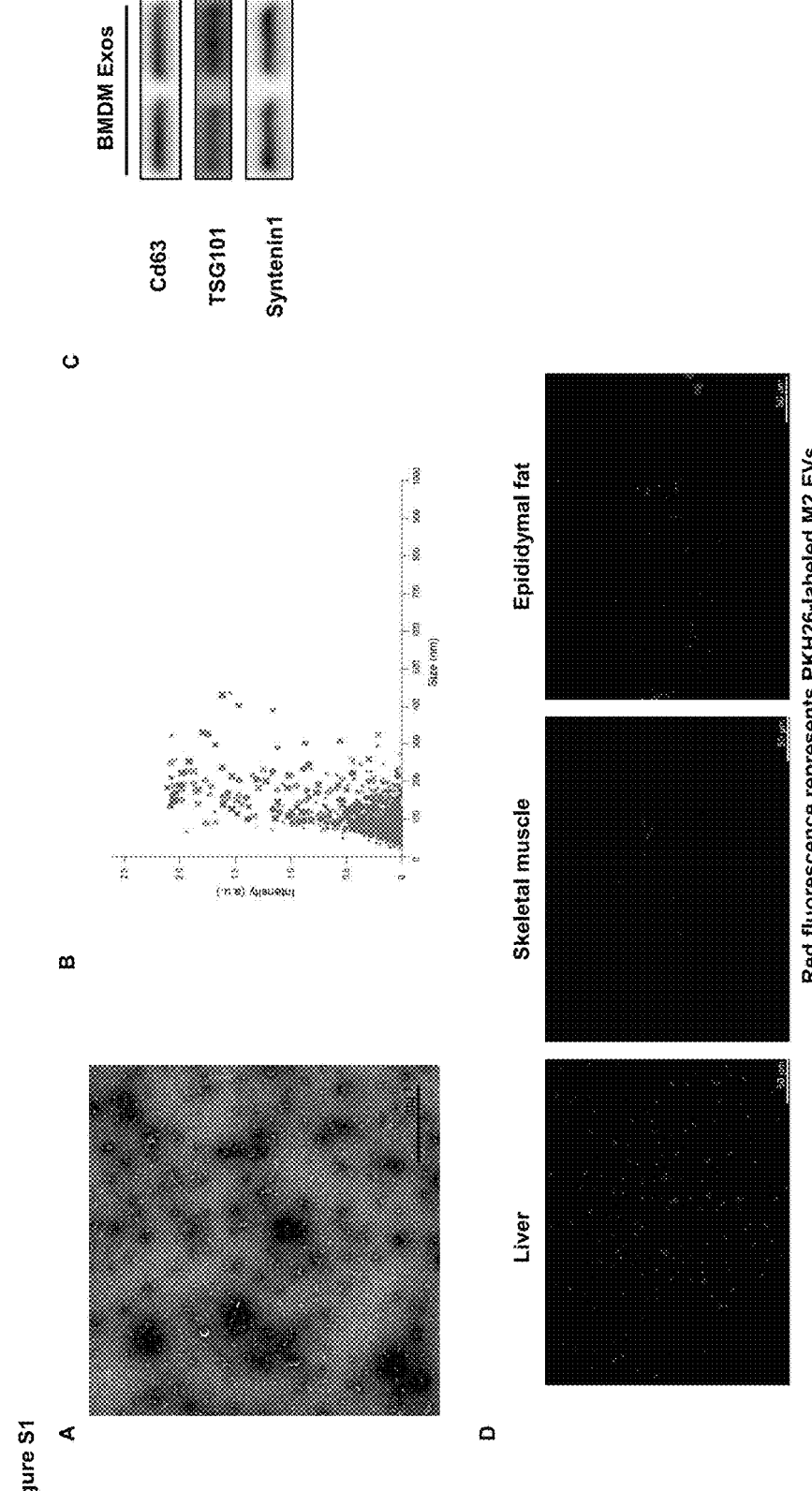
FIGS. 8A-8D. Characteristics of M2 Exos, related to FIG. 1. Electron microscopy analysis (A), NanoSight analysis (B), and expression of EV-associated markers (C) of M2 Exos. (D) The appearance of PKH26 red fluorescence in metabolic tissues after 16 hours intravenous injection of PKH26-labeled M2 Exos.

Anti-Inflammatory Macrophage-Produced Extracellular Vesicles can Attenuate Obesity-Induced Insulin Resistance It was previously shown that Exos harvested from lean mouse eWAT M2-like ATMs can cause improved insulin sensitivity when administrated to obese mice in vivo (Ying et al., 2017). However, because of the relative scarcity of ATMs in lean mice, more in depth mechanism studies are challenging, since it takes 20-25 lean donor mice to harvest enough Exos to treat one recipient mouse. To overcome this, mouse BMDMs were treated with IL4/IL13 to direct them towards an anti-inflammatory M2-like phenotype in vitro. Using a previously reported Exos isolation method (Ying et al., 2017), it was found that M2 Exos are small particles with a diameter of 50-200 nanometer, as measured by electron microscopy and NanoSight analysis (FIGS. 8A and 8B). Additionally, the expression of the exosome-specific markers syntenin1, TSG101, and CD63 were readily detectable in these M2 Exos pellets (FIG. 8C). It was examined whether Exos derived from these IL4/IL13-treated M2-like BMDMs (M2 Exos) can be taken up into peripheral insulin target tissues after intravenous administration to obese mice. After intravenous injection of PKH26-labeled M2 Exos ($1 \times 10^9$ Exos/mouse), robust red fluorescent PKH26 uptake was present in the liver, skeletal muscle, and adipose tissue from obese WT recipients, demonstrating that M2 Exos were readily taken up into these tissues (FIG. 8D).

The effects of these anti-inflammatory M2 Exos on obesity-associated glucose intolerance and insulin resistance were assessed after intravenous injection of M2 Exos into high fat diet (HFD)-fed WT mice ($1 \times 10^9$ Exos/mouse, twice per week). While all recipient mice displayed comparable body weight and glucose-stimulated insulin secretion after 4 weeks treatment (FIGS. 9A and 9B), M2 Exos administration led to a marked improvement in glucose and insulin tolerance (FIGS. 1A and 1B). Additionally, compared to HFD controls, insulin-stimulated AKT phosphorylation was substantially higher in liver, skeletal muscle, and adipose tissue of the obese recipient mice (FIGS. 1C-1E).

Given the marked impact of M2 Exos on in vivo glucose tolerance and insulin sensitivity, the effect of M2 Exos on insulin action in adipocytes, myocytes, and hepatocytes ($1 \times 10^8$ Exos/$0.5 \times 10^6$ cells) was evaluated. It was found that in vitro treatment with M2 Exos led to increased insulin stimulated glucose uptake in both 3T3 adipocytes and L6 myocytes, compared to control cells (FIGS. 2A and 2B). In addition, as shown in FIG. 2C, M2 Exos treatment led to decreased glucagon-stimulated glucose output in primary hepatocytes isolated from HFD/obese mice. M2 Exos treatment also led to increased AKT phosphorylation in adipocytes, myocytes and hepatocytes, consistent with the insulin sensitizing actions of these Exos (FIGS. 2D-2F). Taking together, these results indicate that anti-inflammatory BMDM-derived M2-like Exos mitigate obesity-induced insulin resistance.

miRNAs are Responsible for the M2 Exos Effects

Exos contain a variety of cargoes, including miRNAs, other RNA species, lipids, and proteins (Mathieu et al., 2019). To examine the miRNAs within M2 BMDM Exos with respect to the phenotypes observed, a mouse model was generated with myeloid cell-specific knockout of Dicer, a key ribonuclease responsible of producing mature miRNAs (FIG. 10A). The M2 BMDMs derived from these DicerKO mice produced miRNA-free Exos, as evidenced by non-detectable expression of myeloid cell-specific miR-223 in DicerKO M2 Exos (FIG. 10B). Treatment of 3T3-L1 adipocytes and L6 myocytes with Exos derived from control or DicerKO M2 BMDMs showed that M2 Exos, but not miRNA-depleted Exos, enhanced insulin-stimulated glucose uptake of recipient cells (FIGS. 3A and 3B). The in vivo effects of miRNA-free M2 Exos in obese WT recipient mice was also assessed. After 4 weeks treatment, mice injected with M2 Exos exhibited enhanced insulin sensitivity and glucose tolerance, whereas, miRNA-free M2 Exos treatment had negligible effects on these metabolic responses (FIGS. 3C and 3D). These data suggest that miRNAs are the primary components contributing to the ability of BMDM Exos to enhance insulin sensitivity.

miR-690 Causes Increased Insulin Sensitivity

Given the role of miRNAs within macrophage Exos, the mechanisms by which anti-inflammatory macrophage Exos miRNAs promote insulin sensitivity were explored. The Exos miRNA profile in anti-inflammatory M2-like macrophages was assessed and the top 5 overexpressed miRNAs identified. The anti-inflammatory M2-like BMDMs or RAW264.7 cells expressed much more miR-690, compared to M0 macrophages that were not stimulated with IL4/IL13 (FIG. 11A). In addition, the expression of miR-690 is significantly higher in Exos from these anti-inflammatory M2-like macrophages (FIG. 11B). These results suggested that miR-690 could lead to increased insulin sensitivity.

Figure 4:
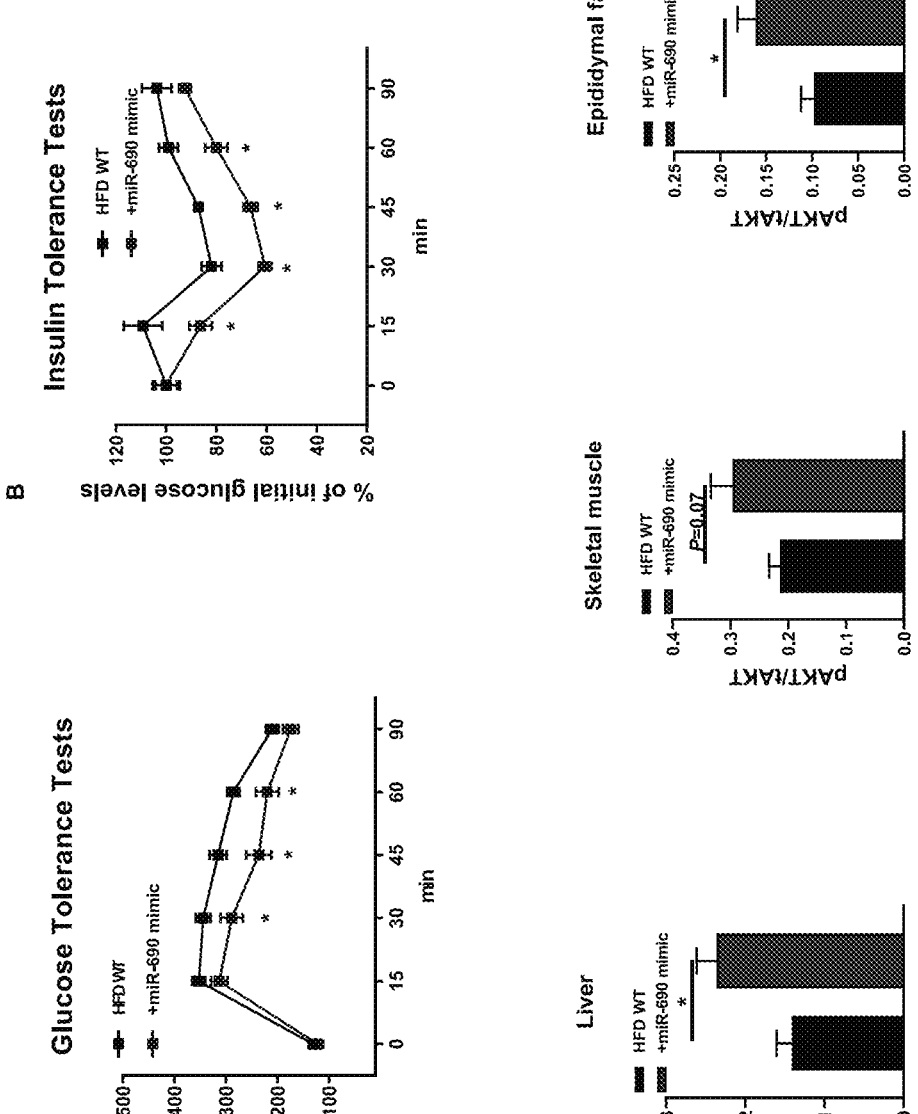
FIGS. 4A-4C. miR-690 improves obesity-induced glucose intolerance and insulin resistance. (A and B) Glucose and insulin tolerance tests of HFD/obese mice after treatment of miR-690 mimic/Invivofectamine. (C) Effect of miR-690 mimic/Invivofectamine on insulin-stimulated AKT phosphorylation of metabolic tissues. Data are presented as mean±SEM. n=6 per group (A-C). *P<0.05, Student's t test.

To explore this, a synthetic cy3 labeled miR-690 mimic was prepared and used to determine whether miR-690 leads to the insulin sensitive phenotypes. To test whether miR-690 exerts insulin sensitizing effects in vivo, the miR-690 mimic was encapsulated using Invivofectamine and intravenously injected into obese recipient mice. The Cy3 labeled miR-690 mimic is efficiently delivered into key metabolic tissues, as shown by appearance of robust Cy3 red fluorescence in the liver, skeletal muscle, and adipose tissue of obese recipients (FIG. 11C). qPCR results confirmed that miR-690 was significantly overexpressed in these tissues after injection of miR-690 mimic (FIG. 11D). After 4 weeks treatment with miR-690 mimic (5 nM/mouse, twice per week), obese mice exhibited significantly improved glucose and insulin tolerance, compared to obese controls injected with empty Invivofectamine (FIGS. 4A and 4B). In addition, in vivo delivery of the miR-690 mimic led to higher levels of insulin-stimulated AKT phosphorylation in liver, skeletal muscle, and adipose tissue of obese recipients, compared to obese controls. These results show that miR-690 promotes insulin signaling (FIG. 4C), indicating its function as an insulin sensitizing miRNA.

Figure 5:
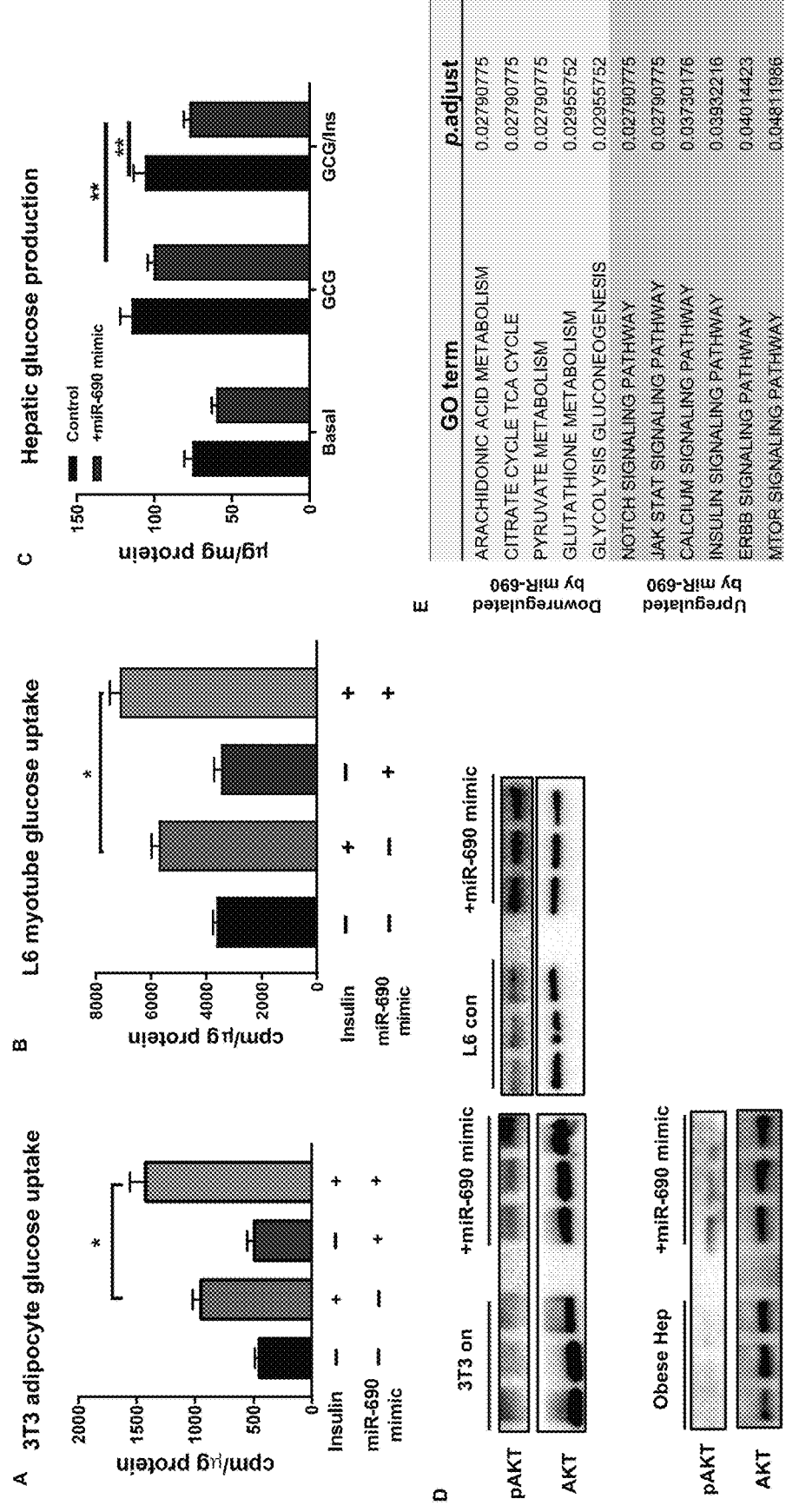
FIGS. 5A-5E. miR-690 enhances cellular insulin sensitivity. Effect of miR-690 mimic on glucose uptake of 3T3-L1 adipocytes (A) and L6 myotubes (B) and hepatic glucose output (C). (D) The insulin-stimulated phosphorylation of AKT after transfection of miR-690 mimic. (E) Pathways in 3T3-L1 adipocytes were upregulated or repressed after overexpression of miR-690. Data are presented as mean±SEM. n=6 per group (A-C, E). *P<0.05, Student's t test.

For in vitro studies, the synthetic miR-690 mimic was used to directly treat 3T3 adipocytes and L6 myocytes and increased insulin stimulated glucose uptake was found in both cell types (FIGS. 5A and 5B; FIG. 12). In addition, the miR-690 mimic treatment led to significantly reduced the glucagon-induced hepatic glucose production in primary hepatocytes from obese mice (FIG. 5C; FIG. 13). Insulin stimulated AKT phosphorylation was also greater in the miR-690 mimic treated cells, consistent with enhanced insulin signaling (FIG. 5D). To further understand the regulatory effects of miR-690 on cellular insulin responses, mRNA sequencing analysis on 3T3-L1 adipocytes was performed. Using gene ontology algorithms, functional annotations of differentially expressed genes between controls and cells transfected with the miR-690 mimic were conducted. As shown in FIG. 5E, overexpression of miR-690 led to upregulation of pathways such as JAK/STAT signaling and insulin signaling with suppression of pathways such as glutathione metabolism.

Figure 6:
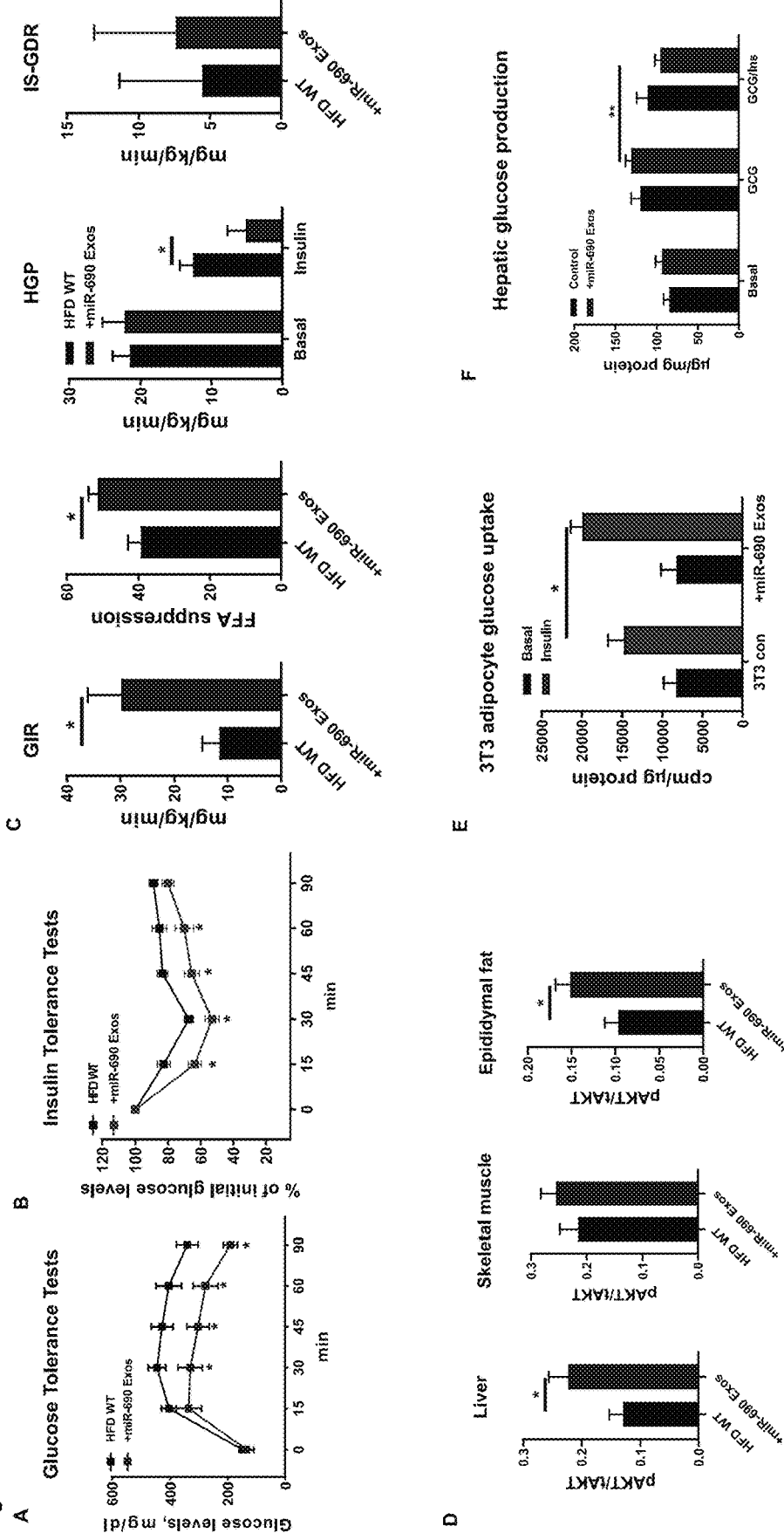
FIGS. 6A-6F. miR-690 enriched Exos can promote insulin sensitivity. (A and B) The glucose tolerance and insulin sensitivity of HFD/obese mice after 5 weeks treatment of either DicerKO miR-690-enriched Exos or control DicerKO Exos. (C) Glucose infusion rate (GIR), the percentage of suppression of free fatty-acid levels (FFA suppression), hepatic glucose production (HGP), and insulin-stimulated glucose disposal rate (IS-GFR) during hyperinsulinemic-euglycemic clamp studies. (D) The levels of insulin-stimulated AKT phosphorylation in liver, skeletal muscle, and epididymal fat of HFD/obese mice treated with miR-690 Exos. Effects of miR-690 Exos on 3T3-L1 adipocyte glucose uptake (E) and hepatic glucose production (F). Data are presented as mean±SEM. n=6 per group (A-F). *P<0.05, Student's t test.

It seemed possible that the uptake and biological effects of these miR-690 containing liposomes might be different if this miR-690 mimic was expressed in natural Exos containing the essential lipid and protein cargoes. Additionally, perhaps miR-690 needs to work in concert with other Exos miRNAs to enhance insulin signaling. To assess these possibilities, the miR-690 mimic was transfected into DicerKO BMDMs which can only produce miRNA free Exos. Exos were then harvested from culture medium of these cells. These Exos were conjugated with latex beads ($1\times10^8$ Exos/ $1\times10^7$ beads). Packaging of the Cy3-miR-690 mimic into these DicerKO BMDM Exos was confirmed as seen by Cy3 red fluorescence upon flow cytometric analyses (FIG. 13A). Additionally, qPCR showed that miR-690 was enriched in DicerKO BMDM Exos after treatment with miR-690 (FIG. 13B). HFD/obese mice were treated with these miR-690 enriched BMDM Exos ($1\times10^9$ Exos/mouse) and the results showed robust delivery to metabolic tissues, as evidenced by the presence of Cy3 red fluorescence in the liver, skeletal muscle, and epididymal fat of obese recipients (FIG. 13C). To evaluate the impact of miR-690 enriched Exos on insulin sensitivity, 10 wks HFD-fed WT mice were injected with either empty or miR-690 enriched BMDM-derived Exos ($1\times10^9$ Exos/mouse, twice per week). After 5 weeks, miR-690 BMDM-derived Exos treatment led to greater accumulation of miR-690 in liver, skeletal muscle, and adipose tissue (FIG. 13D), concomitant with improved glucose and insulin tolerance (FIGS. 6A and 6B). This improvement in in vivo insulin sensitivity was confirmed by hyperinsulinemic-euglycemic clamp studies. We observed higher glucose infusion rates and a greater degree of insulin-mediated suppression of hepatic glucose production and circulating free fatty acid levels (FIG. 6C). However, miR-690 treatment had only a minimal non-significant effect on insulin-stimulated glucose disposal rate (FIG. 6C). Increased insulin-stimulated AKT phosphorylation was observed in liver, skeletal muscle, and adipose tissue (FIG. 6D).

In vitro studies were conducted with 3T3-L1 adipocytes and primary mouse hepatocytes. After coculturing with miR-690 Exos, both 3T3-L1 adipocytes and hepatocytes expressed greater levels of miR-690, compared to control cells (FIG. 13E). 3T3-L1 adipocytes treated with miR-690 Exos showed a significant increase in insulin-stimulated glucose uptake (FIG. 6E). Suppression of hepatic glucose production was also observed in primary hepatocytes from obese mice treated with miR-690 Exos (FIG. 6F). Overall, these results demonstrate that miR-690 contributes to the beneficial effects of anti-inflammatory macrophage Exos on insulin action both in vivo and in vitro.

Figure 7:
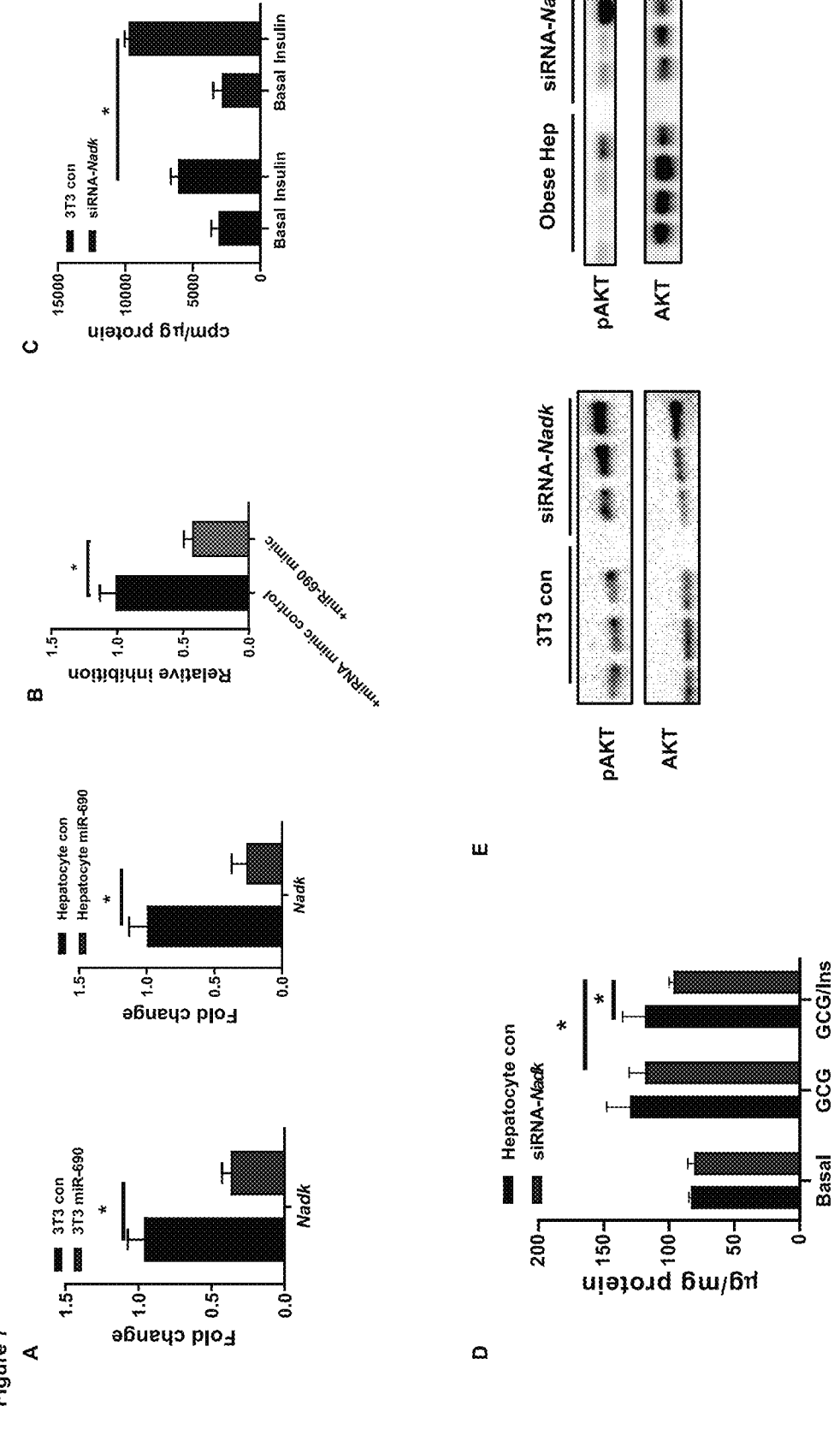
FIGS. 7A-7E. The miR-690-Nadk axis plays a role in mediating cellular insulin responses. (A) Nadk abundance of 3T3-L1 adipocytes and hepatocytes after overexpression of miR-690. (B) Luciferase activity of HEK293 cells after co-transfection of a reporter construct containing 3'UTR region of Nadk with either miRNA mimic control or miR-690 mimic. Effect of siRNA-Nadk on 3T3-L1 glucose uptake (C) and hepatic glucose output (D). (E) The levels of insulin-stimulated AKT phosphorylation after transfection of siRNA-Nadk, Data are presented as mean±SEM. n=6 per group (A-D). *P<0.05, Student's t test.

Nadk is a Target Gene of miR-690 that can Modulate Insulin Signaling miRNAs exert their biological actions by either blocking translation and/or inducing degradation of target mRNAs by seed sequence base-pairing to mRNA recognition sites (Bartel, 2004, 2009). To identify target genes of miR-690, the target gene prediction algorithm TargetScan Mouse 7.2 (Agarwal et al., 2015) was used. Among the tested potential targets, Nadk, a gene encoding NAD+ kinase, was highly repressed in 3T3-L1 adipocytes, L6 myocytes, or primary hepatocytes after overexpression of miR-690 (FIG. 7A). In addition, Nadk expression was significantly reduced in liver, skeletal muscle, and adipose tissue of obese recipients treated with miR-690/Invivofectamine (FIG. 14). To further assess whether Nadk is a genuine target mRNA of miR-690, luciferase reporter assays were performed with a construct containing the 3' untranslated region (UTR) of Nadk containing the miR-690 binding site. After 24 hours co-transfection of this reporter construct and the miR-690 mimic into HEK293 cells, luciferase activity was significantly reduced, compared to control cells transfected only with the Nadk 3'UTR containing luciferase construct (FIG. 7B). Thus, these results suggest that Nadk is a bona fide miR-690 target mRNA.

miR-690-mediated Nadk suppression on cellular insulin sensitivity was evaluated. After knockdown of Nadk expression with short interfering RNAs (siRNA-Nadk), 3T3-L1 adipocytes exhibited increased insulin stimulated glucose uptake (FIGS. 7C). In addition, siRNA-Nadk knockdown in obese mouse hepatocytes led to a reduction in hepatic glucose production after glucagon stimulation (FIG. 7D). It was also observed that Nadk knockdown resulted in increased activation of insulin signaling, as evidenced by higher levels of phosphorylated AKT in cells transfected with siRNA-Nadk (FIG. 7E). Overall, these data demonstrate that the miR-690-Nadk axis plays a role in modulating cellular insulin signaling.

Discussion

Insulin resistance is a major pathophysiologic feature of T2DM and obesity is the most common cause of insulin resistance in man (Johnson and Olefsky, 2013; Kahn et al., 2006; Roden and Shulman, 2019). Indeed, the world-wide obesity epidemic is the main driver of the parallel rise in T2DM prevalence (Ogden et al., 2016). Therefore, a method to enhance insulin sensitivity would have important disease-modifying potential. In this study, it was shown that Exos derived from M2-polarzied BMDMs can attenuate obesity-associated glucose intolerance and insulin resistance. miRNAs are responsible for the beneficial effects of M2 Exos, as evidenced by the minimal effect of miRNA-free BMDM Exos on insulin sensitivity. miR-690, which is highly enriched in BMDM M2 Exos, enhanced insulin action both in vivo and in vitro. Packaging of miR-690 in miRNA deficient DicerKO BMDM Exos restored the beneficial effects of BMDM Exos on glucose tolerance and insulin sensitivity. Finally, it was shown that Nadk is a bona fide target mRNA of miR-690, and that the miR-690-Nadk axis can regulate cellular insulin activity.

Emerging evidence indicates that various types of EV, including exomeres, exosomes, and microvesicles, can serve as circulating vehicles transporting miRNAs into neighboring or distant cells (Mathieu et al., 2019). Previous studies demonstrated that adipose tissue macrophages (ATMs) from insulin sensitive lean mice secrete miRNA-containing EVs which can be transported to insulin target cells where they promote insulin sensitivity (Ying et al., 2017). However, it is challenging to harvest enough macrophages from lean adipose tissues for more in-depth mechanistic studies, because of the small number of ATMs in lean, healthy mice. In these current studies, mouse BMDMs were used as Exos producers. BMDMs were polarized to the anti-inflammatory M2 state by in vitro treatment with IL4/IL13 (Van Dyken and Locksley, 2013; Ying et al., 2013). CM from these cells was used to harvest M2 BMDM Exos according to the ultracentrifugation-based method we previously described (Ying et al., 2017). The majority of vesicles derived from BMDMs were likely exosomes, as evidenced by a diameter of 30-150 nanometers by NanoSight and electron microscopy analysis, and expression of the exosome-associated markers TSG101, Syntenin 1, and CD63 (Koval et al., 2016).

While previous studies report that pro-inflammatory M1-like macrophage derived EVs can blunt cellular insulin sensitivity (Ying et al., 2017; Zhang et al., 2015), the present findings reveal the beneficial, insulin sensitizing, effects of Exos derived from IL4/IL13-stimulated M2-like BMDMs. Given that macrophages residing in lean adipose tissue are largely anti-inflammatory M2-like cells and their Exos have beneficial effect on insulin sensitivity (Lackey and Olefsky, 2016; Ying et al., 2017), BMDMs were stimulated with IL4/IL13 to drive them towards to an anti-inflammatory phenotype. The concept that anti-inflammatory, M2-like, BMDMs-derived Exos can enhance glucose tolerance and insulin sensitivity is supported by both the present in vivo and in vitro data. 4-week treatment of obese/HFD mice with M2 BMDM Exos led to improved glucose intolerance and insulin resistance. In vitro studies showed that treatment with M2 BMDM Exos promoted cellular insulin sensitivity, as demonstrated by increased insulin action on 3T3-L1 adipocyte glucose uptake or hepatic glucose production.

Exos contain a variety of cargo components, including miRNAs, other RNA species, lipids, and proteins (Whitham et al., 2018). Most Exos functions have been attributed to miRNAs that negatively regulate target mRNA expression by binding to specific sequences in the 3'UTR, resulting in mRNA degradation or translation of arrest. Indeed, our results demonstrate that miRNAs within the M2 BMDM Exos are responsible for the insulin sensitizing phenotypes we observed. Thus, miRNA-free M2 BMDM Exos collected from DicerKO BMDMs had negligible effects on insulin sensitivity in both in vivo and in vitro experiments. Consistent with this, Thomou et al. (2017) have shown that DicerKO adipocytes produce miRNA-free Exos which do not regulate gene expression of target cells. Another study by Phinney et al. also supports the key role of miRNAs in the function of mesenchymal stem cell (MSC) Exos, as demonstrated by non-significant effect of DicerKO MSC Exos on macrophage activation (Phinney et al., 2015). In addition, previous studies showed that Exos derived from Drosha-depleted macrophages showed a marked reduction in miRNA content and these Exos had no effect on cellular insulin responses, compared to WT macrophage Exos (Ying et al., 2017).

Previous studies identified the miRNA profile within Exos derived from M2-like lean ATMs (Ying et al., 2017). Among the miRNAs highly enriched in these Exos, we now find that miR-690 functions as a novel insulin sensitizer, since it has beneficial effects on insulin action after in vitro overexpression of miR-690 in either 3T3-L1 adipocytes or hepatocytes. In addition, in vivo delivery of artificial liposomes encapsulating miR-690 shows that these particles are taken up by insulin target tissues, leading to increased expression of miR-690. In vivo treatment with these miR-690 containing liposomes led to improved glucose tolerance and insulin sensitivity in HFD/obese recipient mice. To further validate that miR-690 is responsible for these beneficial metabolic effects in the context of intact Exos, the miR-690 mimic was packaged into DicerKO BMDMD Exos. It was found that in vivo treatment of HFD/obese recipient mice with the miR-690-overexpressing DicerKO BMDM Exos improved liver and adipose tissue insulin sensitivity. These beneficial effects are also supported by in vitro results with DicerKO BMDM Exos treated 3T3-L1 adipocytes and hepatocytes. Together, these data indicate that miR-690 can be largely responsible for the insulin sensitizing effects of M2 Exos.

To further understand the mechanisms underlying the effects of miR-690 on cellular insulin sensitivity, the transcriptome of 3T3-L1 adipocytes overexpressing miR-690 was profiled. This analysis revealed that the miR-690 mimic repress the expression of many mRNAs that are associated with, for example, activation of insulin signaling and repression of glutathione metabolism. Among the mRNAs repressed by miR-690, Nadk, a gene encoding NAD+ kinase that converts nicotinamide adenine dinucleotide (NAD+) to NADP+, was shown to be a bona fide target mRNA of miR-690. The inhibitory effects of NAD+ kinase on cellular insulin action was evidenced by increased in vitro insulin signaling after depletion of Nadk in 3T3-L1 adipocytes and hepatocytes. Previous studies have shown that obesity can reduce NAD+ levels through either repression on NAD+ biosynthesis or increased utilization of NAD+ (Canto et al., 2012; Katsyuba et al., 2020; Stromsdorfer et al., 2016). In addition, Yoshino et al. suggested that treatment with nicotinamide mononucleotide, a NAD+ intermediate, can enhance insulin sensitivity (Yoshino et al., 2018: Yoshino et al., 2011). However, the precise mechanisms by which NAD kinase modulates obesity-associated glucose intolerance and insulin resistance remain to be fully explored.

In summary, M2-polarized BMDM-derived Exos can improve insulin sensitivity. Treatment with M2 Exos leads to enhanced in vivo and in vitro insulin sensitivity, whereas, depletion of Exos miRNAs prevents these effects. miR-690 was identified as an insulin sensitizing miRNA that is highly expressed within M2 Exos, suggesting that this miRNA could become an insulin sensitizing agent for the treatment of metabolic diseases.

In summary, insulin resistance is a major pathophysiologic defect in type 2 diabetes mellitus and obesity weight loss is difficult to achieve and maintain and pharmacologic treatments are unmeted. miR-690 is highly expressed in anti-inflammatory macrophage-derived exosomes and functioned as an insulin sensitizer that can increase insulin action both in vivo and in vitro. As described herein, miR-690 enhanced insulin sensitivity through the suppression of nicotinamide adenine dinucleotide kinase (NADK), and thus may be employed for the treatment of insulin resistance, including type 2 diabetes a or obesity-related insulin resistance.

Example 2

Exemplary Embodiments

In one embodiment, a synthetic delivery vehicle comprising an insulin sensitizing amount of isolated miR-690 is provided. In one embodiment, the delivery vehicle is a nanoparticle or microparticle, e.g., a liposome, and a composition having the vehicle may further comprise a pharmaceutically acceptable carrier.

In one embodiment, a method to inhibit Nadk expression in a mammal is provided comprising: administering to the mammal an effective amount of a composition comprising isolated miR-690 or a vector encoding miR-690.

In one embodiment, a method to inhibit or treat insulin resistance in a mammal is provided comprising administering to the mammal an effective amount of a composition comprising isolated miR-690 or a vector encoding miR-690.

In one embodiment, a method to enhance insulin sensitivity in a mammal is provided, comprising administering to the mammal an effective amount of a composition comprising isolated miR-690 or a vector encoding miR-690.

In one embodiment, a method to treat metabolic disease in a mammal is provided, comprising administering to the mammal an effective amount of a composition comprising isolated miR-690 or a vector encoding miR-690.

In one embodiment, the mammal is a human. In one embodiment, the mammal has type 2 diabetes. In one embodiment, the mammal has obesity-related insulin resistance. In one embodiment, the composition comprises nanoparticles or microparticles. In one embodiment, the composition comprises liposomes. In one embodiment, the vector is a plasmid. In one embodiment, the composition comprises isolated miR-690. In one embodiment, the vector is a recombinant virus.

In one embodiment, the virus is a recombinant adenovirus, retrovirus, lentivirus, herpesvirus or adeno-associated virus.

Various lipids may be employed in liposomes in various weight ratios, e.g., lipids including but not limited to 1,2-dioleoyl-sn-glycero-3-phosphocholine (DOPC), 1,2-dipalmitoyl-sn-glycero-3-phosphocholine (DPPC), 1,2-distearoyl-sn-glycero-3-phosphocholine (DSPC), 1,2-dioleoyl-sn-glycero-3-(phosphor-L-serine] (DOPS), 1,2-dioleoyl-3-trimethylammonium-propane (18:1 DOTAP), 1,2-dioleoyl-sn-glycero-3-phospho-(1'-rac-glycerol) (DOPG), 1,2-dioleoyl-sn-glycero-3-phosphoethanolamine (DOPE), 1,2-dipalmitoyl-sn-glycero-3-phosphoethanolamine (DPPE), 1,2-dioleoyl-sn-glycero-3-phosphoethanolamine-N-[methoxy(polyethylene glycol)-2000] (18:1 PEG-2000 PE), 1,2-dipalmitoyl-sn-glycero-3-phosphoethanolamine-N-[methoxy(polyethylene glycol)-2000] (16:0 PEG-2000 PE), 1-Oleoyl-2-[12-[(7-nitro-2-1,3-benzoxadiazol-4-yl)amino]lauroyl]-sn-Glycero-3-Phosphocholine (18: 1-12:0 NBD PC), 1-palmitoyl-2-{12-[(7-nitro-2-1,3-benzoxadiazol-4-yl)amino]lauroyl}-sn-glycero-3-phosphocholine (16:0-12:0 NBD PC), cholesterol and mixtures/combinations thereof.

In one embodiment, the nano- or micro-particles may have a particle size of less than about 2,000 nm (i.e., 2 microns), less than about 900 nm, less than about 1,800 nm, less than about 1,700 nm, less than about 1,600 nm, less than about 1,500 nm, less than about 1,400 nm, less than about 1,300 nm, less than about 1,200 nm, less than about 1,100 nm, less than about 1,000 nm, less than about 900 nm, less than about 800 nm, less than about 700 nm, less than about 600 nm, less than about 500 nm, less than about 400 nm, less than about 300 nm, less than about 250 nm, less than about 200 nm, less than about 150 nm, less than about 100 nm, less than about 75 nm, or less than about 50 nm, as measured by light-scattering methods, microscopy, or other appropriate methods.

Example 3

Since miR-690 is a potent insulin sensitizer in obese mice and since obesity and insulin resistance are closely connected to the development of nonalcoholic steatohepatitis (NASH), the effect of miR-690 treatment in a mouse NASH model was studied. In humans, NASH is increasingly recognized as a major pathophysiologic syndrome giving rise to cirrhosis and hepatocellular carcinoma and is rapidly becoming the number one cause of liver transplantation. Therefore, attempts to treat or prevent NASH are of medical importance.

Figure 16:
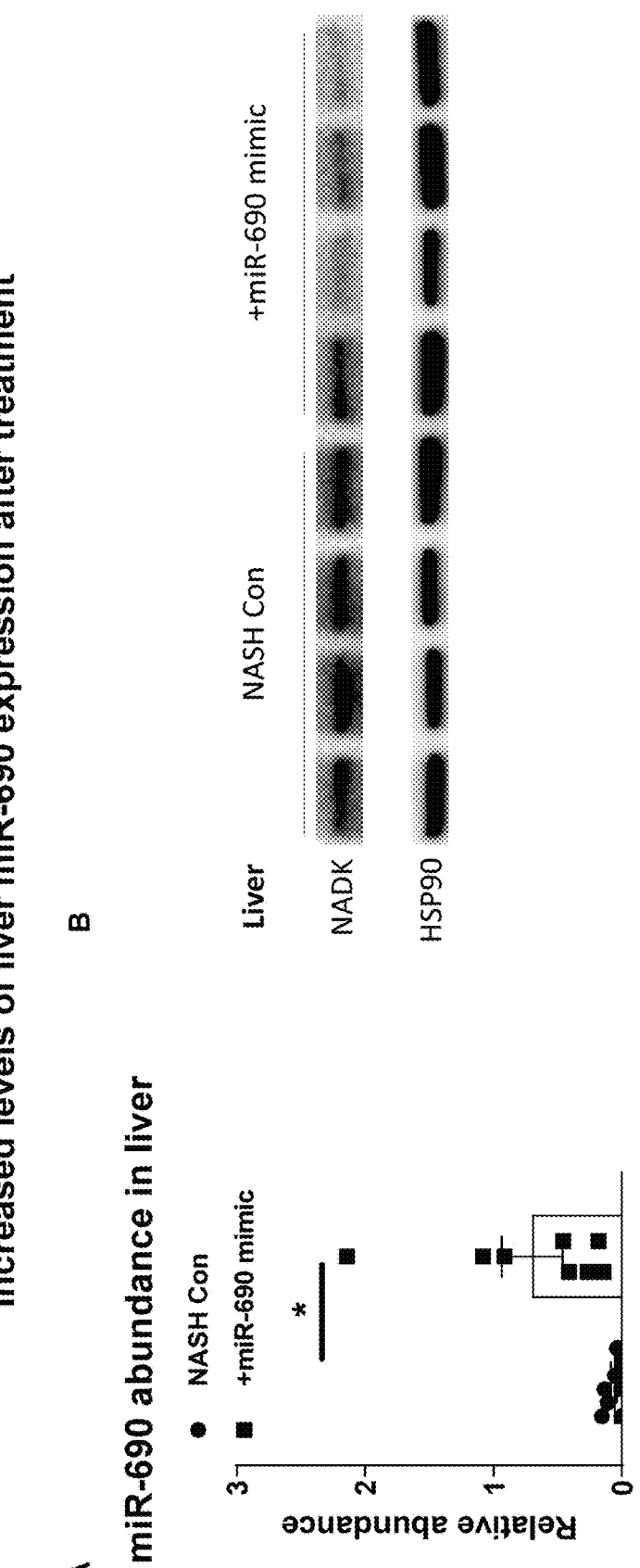
Figure 17:
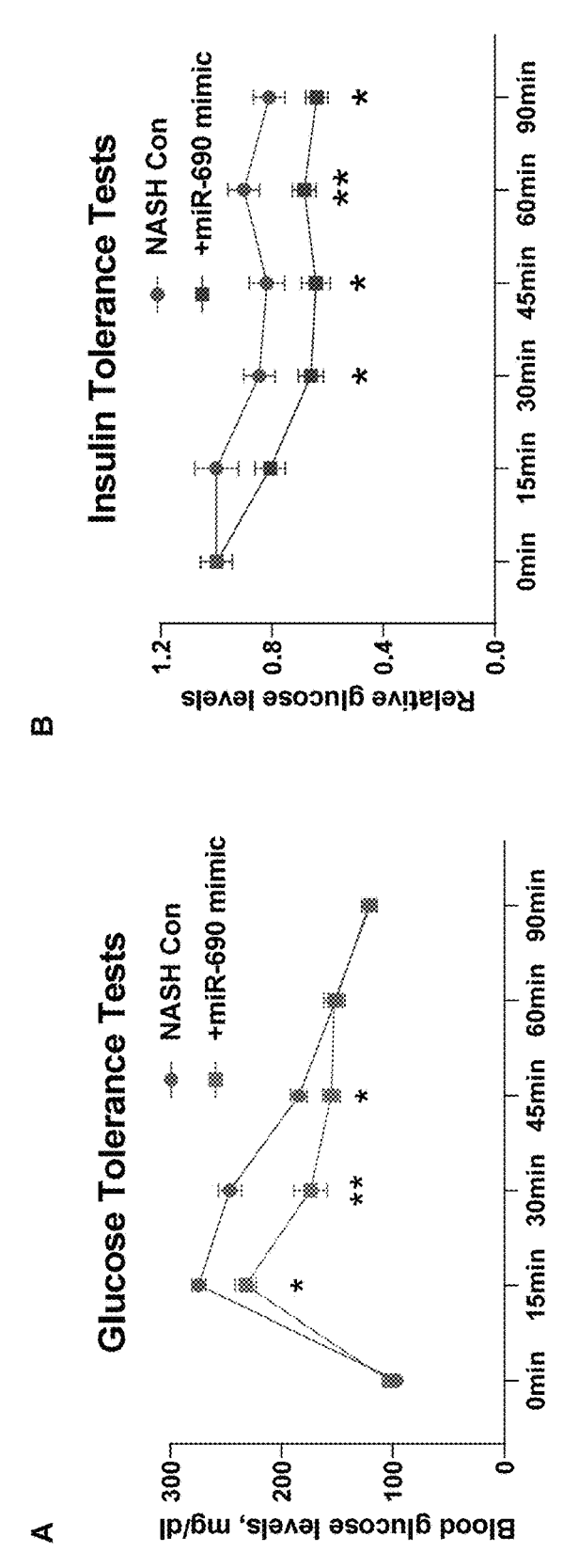
FIGS. 17A-17B. miR-690 treatment promotes glucose tolerance and insulin sensitivity in NASH mice. Glucose tolerance (A) and insulin sensitivity (B) in NASH WT mice after 8 weeks treatment with the nanoparticles containing miR-690 mimic. NASH control mice were treated with the nanoparticles containing scrambled miRNA. Data are presented as mean±SEM. *P<0.05, **P<0.01, Student's t test.

The 3 major components of NASH in both humans and mice are steatosis, hepatic inflammation, and hepatic fibrosis. It is well known that mice placed on a Western diet containing 0.2% cholesterol and sucrose develop nonalcoholic fatty liver disease and then go on to develop NASH in approximately 6 months. This is a well-studied and documented model of human NASH. Mice were placed on the NASH inducing Western diet (WD) for 4 months and at that point they were treated for 8 weeks with biweekly intravenous injections of the miR-690 mimic incorporated into artificial liposomes (FIGS. 15-16). The results were quite positive. The data showed that miR-690 treatment had the expected beneficial effect to improve glucose tolerance and insulin tolerance (FIG. 17).

Figure 18:
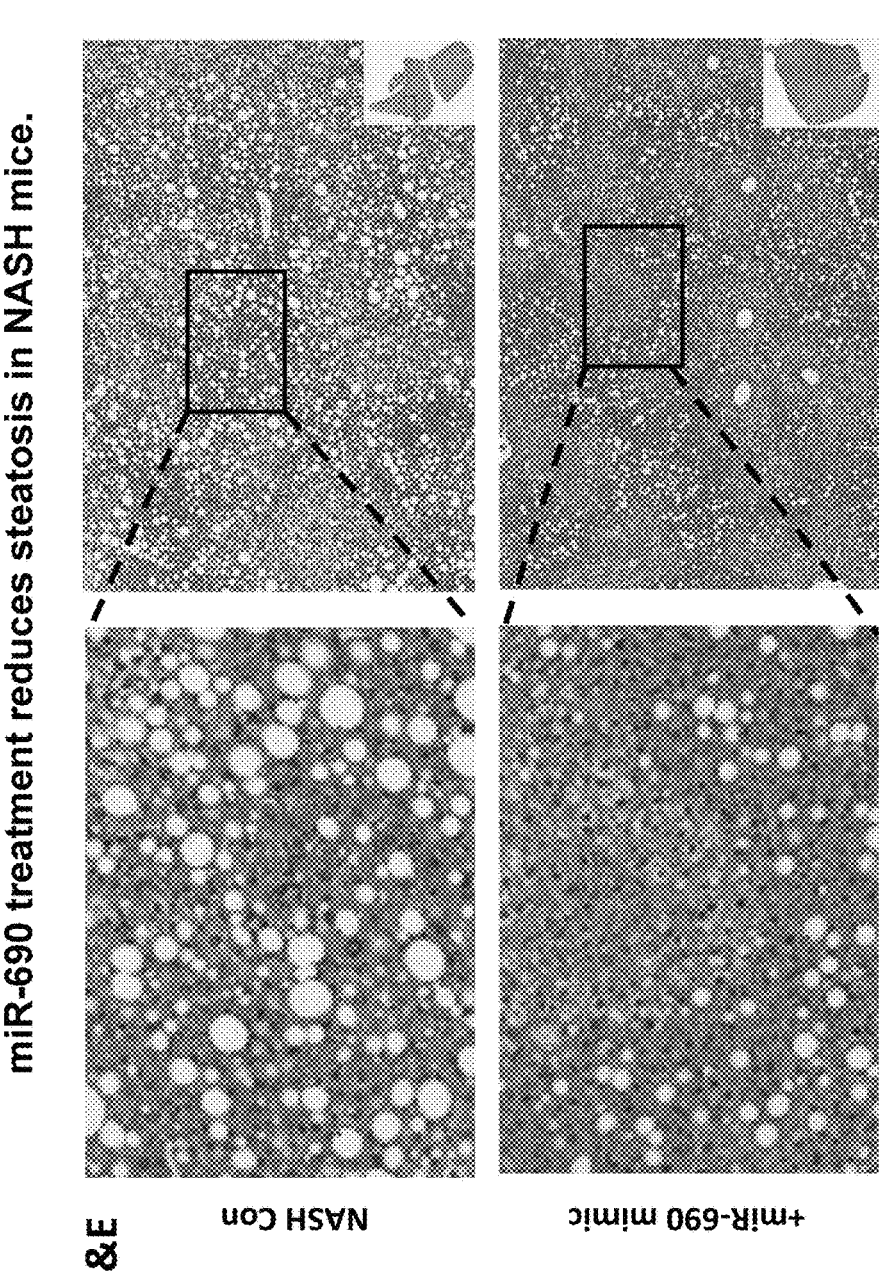
FIG. 18. miR-690 treatment reduces steatosis in NASH mice. H&E staining analysis in the livers of NASH WT mice after 8 weeks treatment with the nanoparticles containing miR-690 mimic. NASH control mice were treated with the nanoparticles containing scrambled miRNA.

At the end of the 8 week treatment period (6 months on WD) mice were sacrificed and the livers were examined. miR-690 treatment led to a substantial decrease in hepatic steatosis as measured by intrahepatic triglyceride levels and H+E staining (FIG. 18, 19A). In addition, gene expression analysis of the treated compared to control livers showed a marked decrease in a variety of genes involved in hepatic de novo lipogenesis, providing an explanation for the antisteatotic effect of miR-690 treatment (FIG. 19B). Furthermore, direct miR-690 treatment of human primary hepatocytes showed large effects to suppress the de novo lipogenesis program and greatly inhibited expression of NADK, which is the target of miR-690 (FIG. 19C).

Figure 22:
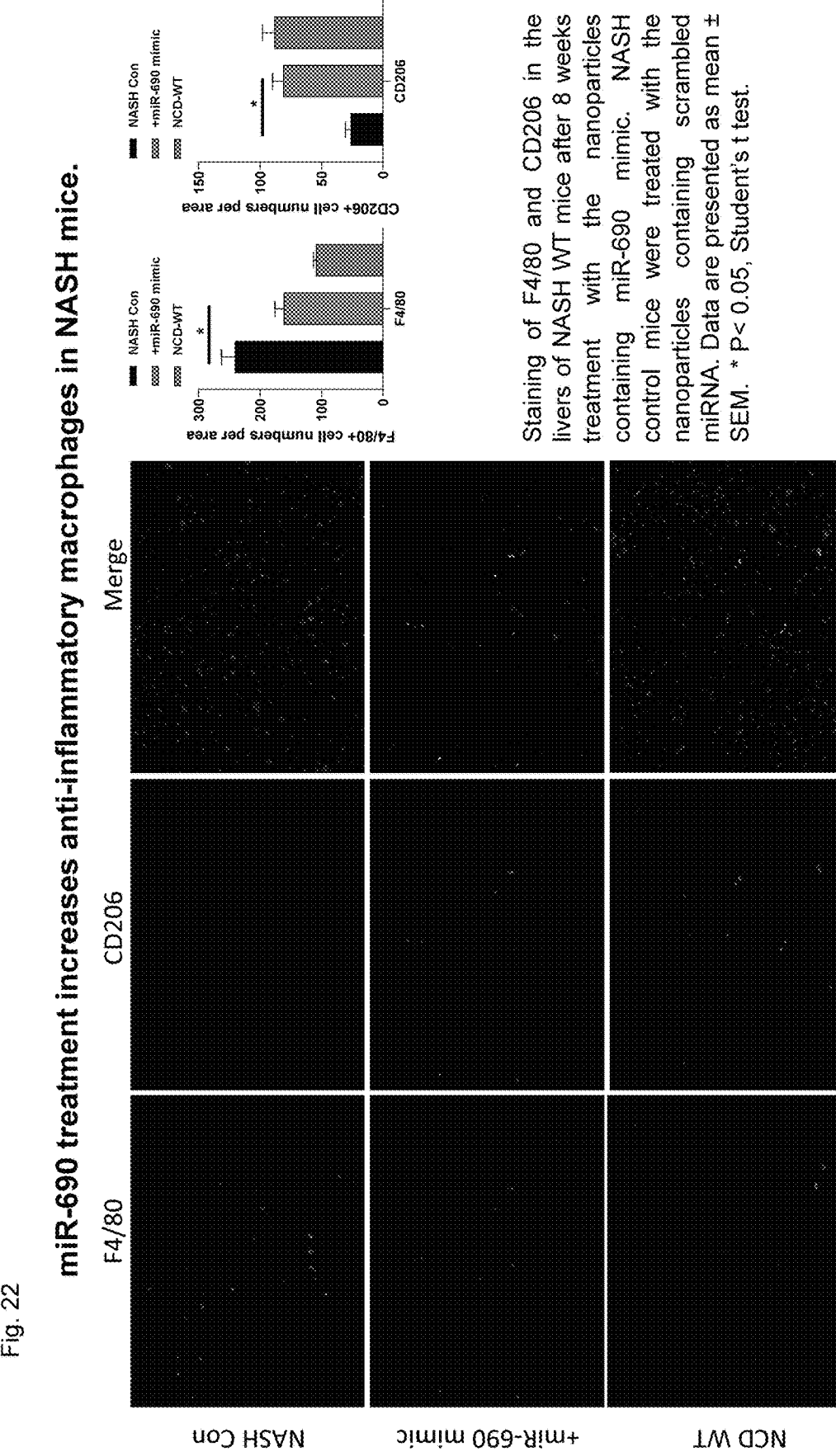
FIG. 22. miR-690 treatment increases anti-inflammatory macrophages in NASH mice. Staining of F4/80 and CD206 in the livers of NASH WT mice after 8 weeks treatment with the nanoparticles containing miR-690 mimic. NASH control mice were treated with the nanoparticles containing scrambled miRNA. Data are presented as mean±SEM. * P<0.05, Student's t test FIG. 23. miR-690 treatment reduces fibrosis in NASH mice. Sirius red staining analysis of the livers from NASH WT mice after 8 weeks treatment with the nanoparticles containing miR-690 mimic. NASH control mice were treated with the nanoparticles containing scrambled miRNA. Data are presented as mean±SEM. **P<0.01, Student's t test.

Inflammation is another major manifestation in NASH livers and miR-690 treatment was highly effective at reversing the hepatic inflammatory phenotype (FIG. 20). When the livers were stained for Clec4f (a known specific marker of Kupffer cells (KCs) in the liver) staining was diminished in the NASH mice treated with empty liposomes but was markedly increased after miR-690 treatment (FIG. 21). Indeed, Clec4f staining in the miR-690 treated mice was now comparable to that seen in lean chow fed mice (NCD). This is highly consistent with the biology of Clec4f as a KC marker. Thus, it is already known that during the development of NASH, resident KCs undergo apoptosis and are replaced by freshly recruited monocytes which differentiate into hepatic macrophages and then become KC-like cells. Interestingly, Clec4f mRNA expression levels are reduced in NASH KCs and KC-like cells, consistent with the lower levels of staining of Clec4f in the NASH livers (FIG. 21). Remarkably, after miR-690 treatment, Clec4f staining increased dramatically, indicative of "healthy" KCs that are active in tissue homeostasis and repair (FIG. 21). This would represent a beneficial effect of miR-690 treatment in NASH. The livers were also stained for F4/80, which is a well-known surface marker for both KCs and freshly recruited monocytes/macrophages. In the empty liposome treated mice there are many red staining cells F4/80 cell comprising of both KC and RHM populations (FIG. 21). After miR-690 treatment the number of F4/80+ staining cells is substantially reduced indicating a much lower number of recruited macrophages. Indeed, almost all of the remaining F4/80+ cells in the miR-690 treated mice are also positive for Clec4f staining demonstrating their identity as KCs. Additionally, miR-690 treatment led to an increased number of macrophages staining positive in the livers for the anti-inflammatory marker CD206 (FIG. 22). The results in the miR-690 treated WD mice are quite comparable to those seen in normal chow fed mice livers.

Figure 23:
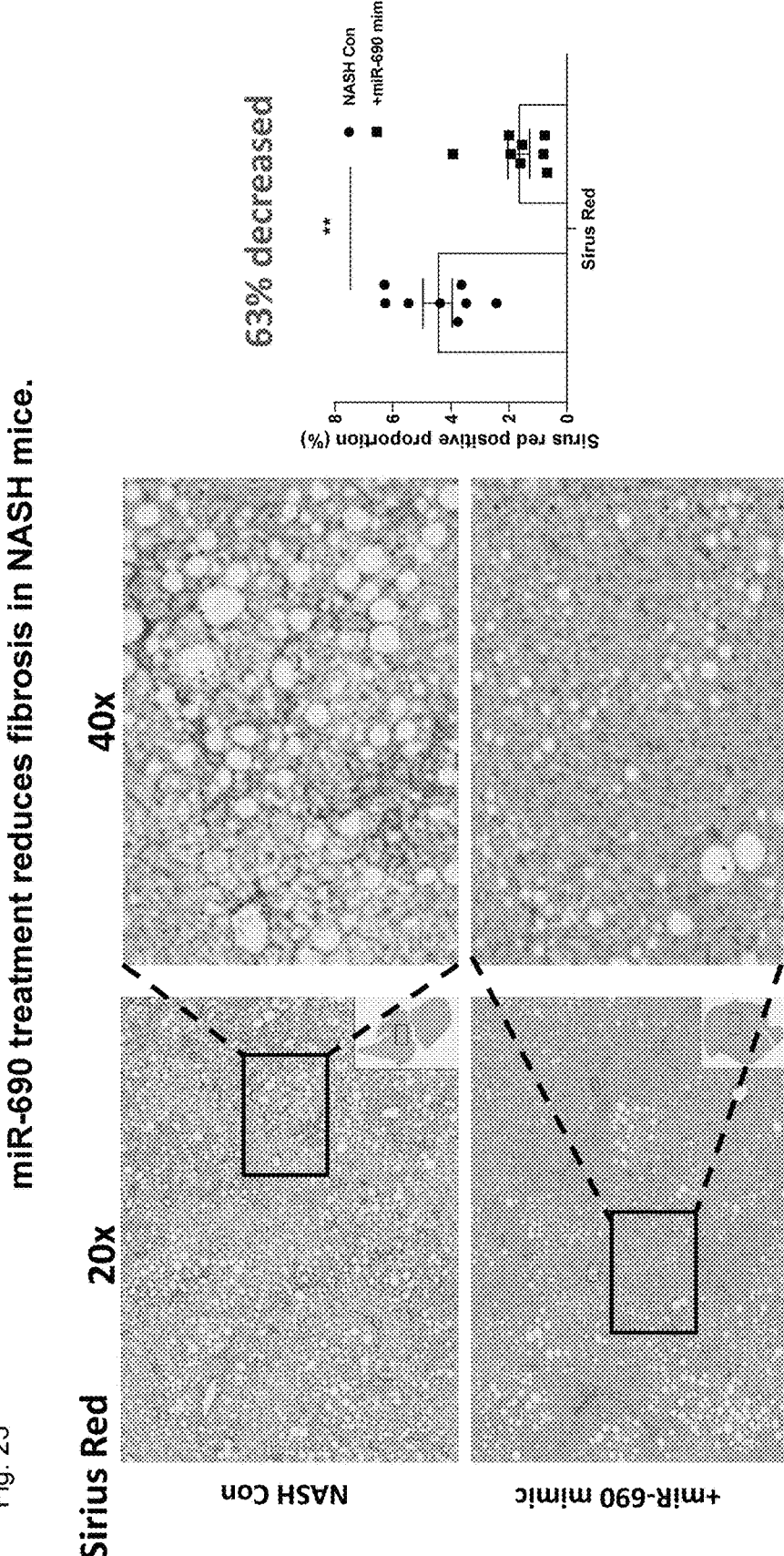
Figure 24:
FIG. 24. Histology analysis of liver samples. The fibrosis score in NASH WT mice after 8 weeks treatment with the nanoparticles containing miR-690 mimic. NASH control mice were treated with the nanoparticles containing scrambled miRNA. Data are presented as mean±SEM. **P<0.01, Student's t test.

The livers were also examined for the degree of fibrosis. As seen in FIGS. 23-24 the empty liposome WD treated mice exhibited the expected and marked increase in sirius red staining for collagen. The miR-690 treated WD mice showed a >80% reduction in sirius red collagen staining which is an extremely robust anti-NASH effect. In support of this finding, miR-690 treatment repressed the expression of key genes associated with liver fibrosis (FIG. 25). In summary, miR-690 treatment led a decrease in all 3 of the major pathophysiologic components of NASH, steatosis, inflammation, and fibrosis. These results indicate that miR-690 treatment could become an important new anti-NASH therapeutic.

References

Agarwal, V., Bell, G. W., Nam, J. W., and Bartel, D. P. (2015). Predicting effective microRNA target sites in mammalian mRNAs. Elite 4.

Bartel, D. P. (2004). MicroRNAs: genomics, biogenesis, mechanism, and function. Cell 116, 281-297.

Bartel, D. P. (2009). MicroRNAs: target recognition and regulatory functions. Cell 136, 215-233.

Canto, C., Houtkooper, R. H., Pirinen, E., Youn, D. Y., Oosterveer, M. H., Cen, Y., Fernandez-Marcos, P. J., Yamamoto, H., Andreux, P. A., Cettour-Rose, P., et al. (2012). The NAD(+) precursor nicotinamide riboside enhances oxidative metabolism and protects against high-fat diet-induced obesity. Cell Metab 15, 838-847.

Crewe, C., Joffin, N., Rutkowski, J. M., Kim, M., Zhang, F., Towler, D. A., Gordillo, R., and Scherer, P. E. (2018). An Endothelial-to-Adipocyte Extracellular Vesicle Axis Governed by Metabolic State. Cell 175, 695-708 e613.

den Boer, M. A., Voshol, P. J., Schroder-van der Elst, J. P., Korsheninnikova, E., Ouwens, D. M., Kuipers, F., Havekes, L. M., and Romijn, J. A. (2006), Endogenous interleukin-10 protects against hepatic steatosis but does not improve insulin sensitivity during high-fat feeding in mice, Endocrinology 147, 4553-4558.

Fink, L. N., Costford, S. R., Lee, Y. S., Jensen, T. E., Bilan, P. J., Oberbach, A., Bluher, M., Olefsky, J. M., Sams, A., and Klip, A. (2014). Pro-inflammatory macrophages increase in skeletal muscle of high fat-fed mice and correlate with metabolic risk markers in humans. Obesity (Silver Spring) 22, 747-757.

Guay, C., Kruit, J. K., Rome, S., Menoud, V., Mulder, N. L., Jurdzinski, A., Mancarella, F., Sebastiani, G., Donda, A., Gonzalez, B. J., et al. (2019). Lymphocyte-Derived Exosomal MicroRNAs Promote Pancreatic beta Cell Death and May Contribute to Type 1 Diabetes Development. Cell Metab 29, 348-361 e346.

Hotamisligil, G. S. (2017). Inflammation, metaflammation and immunometabolic disorders. Nature 542, 177-185.

Hotamisligil, G. S., Arner, P., Caro, J. F., Atkinson, R. L., and Spiegelman, B. M. (1995). Increased adipose tissue expression of tumor necrosis factor-alpha in human obesity and insulin resistance. J Clin Invest 95, 2409-2415.

Hotamisligil, G. S., Peraldi, P., Budavari, A., Ellis, R., White, M. F., and Spiegelman, B. M. (1996). IRS-1-mediated inhibition of insulin receptor tyrosine kinase activity in TNF-alpha- and obesity-induced insulin resistance. Science 271, 665-668.

Johnson, A. M., and Olefsky, J. M. (2013). The origins and drivers of insulin resistance. Cell 152, 673-684.

Kahn, S. E., Hull, R. L., and Utzschneider, K. M. (2006). Mechanisms linking obesity to insulin resistance and type 2 diabetes. Nature 444, 840-846.

Kanda, H., Tateya, S., Tamori, Y., Kotani, K., Hiasa, K., Kitazawa, R., Kitazawa, S., Miyachi, H., Maeda, S., Egashira, K., et al (2006). MCP-1 contributes to macrophage infiltration into adipose tissue, insulin resistance, and hepatic steatosis in obesity. J Clin Invest 116, 1494-1505.

Kang, K., Reilly, S. M., Karabacak, V., Gangl, M. R., Fitzgerald, K., Hatano, B., and Lee. C. H. (2008). Adipocyte-derived Th2 cytokines and myeloid PPARdelta regulate 2macrophage polarization and insulin sensitivity. Cell Metab 7, 485-495.

Katsyuba, E., Romani, M., Hofer, D., and Auwerx, J. (2020). NAD+ homeostasis in health and disease. Nature Metabolism 2, 9-31.

Kowal, J., Arras, G., Colombo, M., Jouve, M., Morath, J. P., Primdal-Bengtson, B., Dingli, F., Loew, D., Tkach, M., and Thery, C. (2016). Proteomic comparison defines novel markers to characterize heterogeneous populations of extracellular vesicle subtypes. Proc Natl Acad Sci U S A 113, E968-977.

Kratz, M., Coats, B. R., Hisert, K. B., Hagman, D., Mutskov, V., Pens, E., Schoenfelt, K. Q., Kuzma, J. N., Larson, I., Billing, P. S., et al. (2014). Metabolic dysfunction drives a mechanistically distinct proinflammatory phenotype in adipose tissue macrophages. Cell Metab 20, 614-625.

Lackey, D. E., and Olefsky, J. M. (2016). Regulation of metabolism by the innate immune system. Nat Rev Endocrinol 12, 15-28.

Lee, Y. S., Wollam, J., and Olefsky, J. M. (2018). An Integrated View of Immunometabolism, Cell 172, 22-40.

Li, P., Liu, S., Lu, M., Bandyopadhyay, G., Oh, D., Imamura, T., Johnson, A. M. F., Sears, D., Shen, Z., Cui, B., et al. (2016). Hematopoietic-Derived Galectin-3 Causes Cellular and Systemic Insulin Resistance, Cell 167, 973-984 e912.

Li, P., Oh, D. Y., Bandyopadhyay, G., Lagakos, W. S., Talukdar, S., Osborn, O., Johnson, A., Chung, H., Maris, M., Ofrecio, J. M., et al. (2015). LTB4 promotes insulin resistance in obese mice by acting on macrophages, hepatocytes and myocytes. Nat Med 21, 239-247.

Lumeng, C. N., Bodzin, J. L., and Saltiel, A. R. (2007a). Obesity induces a phenotypic switch in adipose tissue macrophage polarization. J Clin Invest 117, 175-184.

Lumeng, C. N., Deyoung, S. M., Bodzin, J. L., and Saltiel, A. R. (2007b). Increased inflammatory properties of adipose tissue macrophages recruited during diet-induced obesity. Diabetes 56, 16-23.

Mathieu, M., Martin-Jaular, L., Lavieu, G., and Thery, C. (2019). Specificities of secretion and uptake of exosomes and other extracellular vesicles for cell-to-cell communication. Nat Cell Biol 21, 9-17.

Morinaga, H., Mayoral, R., Heinrichsdorff, J., Osborn, O., Franck, N., Hah, N., Walenta, E., Bandyopadhyay, G., Pessentheiner, A. R., Chi, T. J., et al. (2015). Characterization of distinct subpopulations of hepatic macrophages in HFD/obese mice. Diabetes 64, 1120-1130.

Odegaard, J. I., Ricardo-Gonzalez, R. R., Goforth, M. H., Morel, C. R., Subramanian, V., Mukundan, L., Red Eagle, A., Vats, D., Brombacher, F., Ferrante, A. W., et al. (2007). Macrophage-specific PPARgamma controls alternative activation and improves insulin resistance. Nature 447, 1116-1120.

Ogden, C. L., Carroll, M. D., Lawman, H. G., Fryar, C. D., Kruszon-Moran, D., Kit, B. K., and Flegal, K. M. (2016). Trends in Obesity Prevalence Among Children and Adolescents in the United States, 1988-1994 Through 2013-2014. JAMA 315, 2292-2299.

Phinney, D. G., Di Giuseppe, M., Njah, J., Sala, E., Shiva, S., St Croix, C. M., Stolz, D. B., Watkins, S. C., Di, Y. P., Leikauf, G. D., et al. (2015). Mesenchymal stem cells use extracellular vesicles to outsource mitophagy and shuttle microRNAs. Nat Commun 6, 8472.

Qiu, Y., Nguyen, K. D., Odegaard, J. I., Cui, X., Tian, X., Locksley, R. M., Palmiter, R. D., and Chawla, A. (2014). Eosinophils and type 2 cytokine signaling in macrophages orchestrate development of functional beige fat. Cell 157, 1292-1308.

Rajbhandari, P., Thomas, B. J., Feng, A. C., Hong, C., Wang, J., Vergnes, L., Sallam, T., Wang, B., Sandhu, J., Seldin, M. M., et al. (2018). IL-10 Signaling Remodels Adipose Chromatin Architecture to Limit Thermogenesis and Energy Expenditure. Cell 172, 218-233 e217.

Roden, M., and Shulman, G. I. (2019). The integrative biology of type 2 diabetes. Nature 576, 51-60.

Romeo, G. R., Lee, J., and Shoelson, S. E. (2012). Metabolic syndrome, insulin resistance, and roles of inflammation-mechanisms and therapeutic targets. Arterioscler Thromb Vasc Biol 32, 1771-1776.

Saltiel, A. R., and Olefsky, J. M. (2017). Inflammatory mechanisms linking obesity and metabolic disease. J Clin Invest 127, 1-4.

Saraiva, M., and O'Garra, A. (2010). The regulation of IL-10 production by immune cells. Nat Rev Immunol 10, 170-181.

Stromsdorfer, K. L., Yamaguchi, S., Yoon, M. J., Moseley, A. C., Franczyk, M. P., Kelly, S. C., Qi, N., Imai, S., and Yoshino, J. (2016). NAMPT-Mediated NAD(+) Biosynthesis in Adipocytes Regulates Adipose Tissue Function and Multi-organ Insulin Sensitivity in Mice. Cell Rep 16, 1851-1860.

Thomou, T., Mori, M. A., Dreyfuss, J. M., Konishi, M., Sakaguchi, M., Wolfrum, C., Rao, T. N., Winnay, J. N., Garcia-Martin, R., Grinspoon, S. K., et al. (2017). Adipose-derived circulating miRNAs regulate gene expression in other tissues. Nature 542, 450-455.

Tiemessen, M. M., Jagger, A. L., Evans, H. G., van Herwijnen, M. J., John, S., and Taams, L. S. (2007). CD4+ CD25+Foxp3+ regulatory T cells induce alternative activation of human monocytes/macrophages. Proc Natl Acad Sci U S A 104, 19446-19451.

Van Dyken, S. J., and Locksley, R. M. (2013). Interleukin-4- and interleukin-13-mediated alternatively activated macrophages: roles in homeostasis and disease. Annu Rev Immunol 31, 317-343.

Weisberg, S. P., McCann, D., Desai, M., Rosenbaum, M., Leibel, R. L., and Ferrante, A. W., Jr. (2003). Obesity is associated with macrophage accumulation in adipose tissue. J Clin Invest 112, 1796-1808.

Whitham, M., Parker, B. L., Friedrichsen, M., Hingst, J. R., Hjorth, M., Hughes, W. E., Egan, C. L., Cron, L., Watt, K. I., Kuchel, R. P., et al. (2018). Extracellular Vesicles Provide a Means for Tissue Crosstalk during Exercise. Cell Metab 27, 237-251 e234.

Wu, D., Molofsky, A. B., Liang, H. E., Ricardo-Gonzalez, R. R., Jouihan, H. A., Bando, J. K., Chawla, A., and Locksley, R. M. (2011). Eosinophils sustain adipose alternatively activated macrophages associated with glucose homeostasis. Science 332, 243-247.

Xu, X., Grijalva, A., Skowronski, A., van Eijk, M., Serlie, M. J., and Ferrante, A. W., Jr. (2013). Obesity activates a program of lysosomal-dependent lipid metabolism in adipose tissue macrophages independently of classic activation. Cell Metab 18, 816-830.

Ying, W., Cheruku, P. S., Bazer, F. W., Safe, S. H., and Zhou, B. (2013). Investigation of macrophage polarization using bone marrow derived macrophages. J Vis Exp.

Ying, W., Riopel, M., Bandyopadhyay, G., Doug, Y., Birmingham, A., See, J. B., Ofrecio, J. M., Wollam, J., Hernandez-Carretero, A., Fu, W., et al. (2017). Adipose Tissue Macrophage-Derived Exosomal miRNAs Can Modulate In Vivo and In Vitro Insulin Sensitivity. Cell 171, 372-384 e312.

Yoshino, J., Baur, J. A., and Imai, S. I. (2018). NAD(+) Intermediates: The Biology and Therapeutic Potential of NMN and NR. Cell Metab 27, 513-528.

Yoshino, J., Mills, K. F., Yoon, M. J., and Imai, S. (2011). Nicotinamide mononucleotide, a key NAD(+) intermediate, treats the pathophysiology of diet- and age-induced diabetes in mice. Cell Metab 14, 528-536.

Zhang, Y., Shi, L., Mei, H., Zhang, J., Zhu, Y., Han, X., and Zhu, D. (2015). Inflamed macrophage microvesicles induce insulin resistance in human adipocytes. Nutr Metab (Lond) 12, 21.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A synthetic delivery vehicle comprising an insulin sensitizing amount of isolated miR-690 optionally comprising a pharmaceutically acceptable carrier.

2. The delivery vehicle of claim 1 which is a nanoparticle or microparticle or liposome.

3. The delivery vehicle of claim 2 which comprises one or more of DC-cholesterol, 1,2-dioleoyl-sn-glycero-3-phosphoethanolamine, an ionizable cationic lipid or a lipidoid.

4. The delivery vehicle of claim 1 which comprises about 0.01 mg to about 50 mg, 0.5 mg to about 20 mg, or 1 mg to about 10 mg, of the isolated miR-690.

5. The delivery vehicle of claim 1 which comprises any one of SEQ ID Nos. 1-9 or a nucleotide sequence with at least 90% nucleotide sequence identity thereto.

6. A method to inhibit or treat insulin resistance, to enhance insulin sensitivity, to treat metabolic disease, or to inhibit Nadk expression, in a mammal, comprising administering to the mammal an effective amount of a composition comprising isolated miR-690 or a vector encoding miR-690.

7. The method of claim 6 wherein the mammal is a human.

8. The method of claim 6, wherein the mammal has type 2 diabetes, obesity-related insulin resistance, nonalcoholic liver disease, polycystic ovarian syndrome or is obese.

9. The method of claim 6 wherein the composition comprises nanoparticles or microparticles or liposomes.

10. The method of claim 6 wherein the composition comprises a plasmid encoding miR-690, isolated miR-690 or a recombinant virus encoding miR-690.

11. The method of claim 10 wherein the virus is a recombinant adenovirus, retrovirus, lentivirus, herpesvirus or adeno-associated virus.

12. The method of claim 6 wherein the amount reduces steatosis, reduces hepatic inflammation, or reduces hepatic fibrosis.

13. The method of claim 6, wherein the composition is injected or is systemically, locally, intravenously, topically, subcutaneously, intramuscularly, or orally administered.

14. The method of claim 6 wherein the composition comprises nanoparticles or microparticles comprising the isolated miR-690 or the vector encoding miR-690.

15. The method of claim 14 wherein the nanoparticles or microparticles comprise a liposome.

16. The method of claim 15 which comprises one or more of DC-cholesterol, 1,2-dioleoyl-sn-glycero-3-phosphoethanolamine, an ionizable cationic lipid or a lipidoid.

17. The method of claim 6 wherein the composition further comprises a pharmaceutically acceptable carrier.

18. The method of claim 6 wherein the composition comprises about 0.01 mg to about 50 mg, about 0.5 mg to about 20 mg or about 1 mg to about 10 mg, of the isolated miR-690.

19. The method of claim 6 wherein the composition comprises any one of SEQ ID Nos. 1-9 or a nucleotide sequence with at least 90% nucleotide sequence identity thereto.

20. The method of claim 6, wherein the metabolic disease is Type 2 Diabetes.

\* \* \* \* \*